(12) United States Patent
Wu et al.

(10) Patent No.: US 8,143,399 B2
(45) Date of Patent: *Mar. 27, 2012

(54) PHOTOSENSITIZER DYE

(75) Inventors: Chun-Guey Wu, Hualien County (TW);
Chia-Yuan Chen, Chiayi (TW);
Shi-Jhang Wu, Taipei County (TW);
Jheng-Ying Li, Taoyuan County (TW)

(73) Assignee: National Central University, Taoyuan (TW)

( * ) Notice: Subject to any disclaimer, the term of this patent is extended or adjusted under 35 U.S.C. 154(b) by 571 days.

This patent is subject to a terminal disclaimer.

(21) Appl. No.: 12/356,076

(22) Filed: Jan. 20, 2009

(65) Prior Publication Data
US 2009/0209762 A1 Aug. 20, 2009

Related U.S. Application Data

(63) Continuation-in-part of application No. 12/125,939, filed on May 23, 2008, now Pat. No. 7,645,879.

(30) Foreign Application Priority Data

Feb. 19, 2008 (TW) .............................. 97105782 A
Dec. 12, 2008 (TW) .............................. 97148638 A

(51) Int. Cl.
*C07F 15/00* (2006.01)
*B01J 31/12* (2006.01)
(52) U.S. Cl. .......................................... 546/2; 502/167
(58) Field of Classification Search ....... 546/2; 502/167
See application file for complete search history.

(56) References Cited

U.S. PATENT DOCUMENTS

| 6,245,988 | B1 | 6/2001 | Gratzel et al. |
| 6,639,037 | B2 | 10/2003 | Van Swieten et al. |
| 7,321,037 | B2 | 1/2008 | Wu et al. |
| 7,645,879 | B2 * | 1/2010 | Wu et al. ........................... 546/2 |
| 2007/0000539 | A1 | 1/2007 | Gui et al. |
| 2007/0017569 | A1 | 1/2007 | Gui et al. |

FOREIGN PATENT DOCUMENTS

| JP | 2002-105346 | 4/2002 |
| JP | 2007-302879 | 11/2007 |
| TW | 200742758 | 11/2007 |
| WO | 2007091525 | 8/2007 |
| WO | 2009020098 | 2/2009 |

OTHER PUBLICATIONS

Gao, F. et al.: A new heteroleptic ruthenium sensitizer enhances the absorptivity of mesoporous titania film for a high efficiency dye-sensitized solar cell. Chem. Commun., vol. 23, pp. 2635-2637, 2008.*
Chen, C-Y. et al.: Multifunctionalized Ruthenium-based supersensitizers for highly efficient dye-sensitized solar cells. Angew Chem. vol. 47, pp. 7342-7345, 2008.*
"Office Action of Australia Counterpart Application," Issued on Jun. 21, 2010, p. 1-p. 2, in Which the Listed References Were was Cited.
"Office Action of Taiwan Counterpart Application", issued on Jul. 20, 2011, p. 1-p. 4, in which the listed reference was cited.
Chen et al., "A New Route to Enhance the Light-Harvesting Capability of Ruthenium Complexes for Dye-Sensitized Solar Cells", *Advanced Materials*, vol. 19, No. 22, issued on 2007, pp. 3888-3891.
Gao et al., "A new heteroleptic ruthenium sensitizer enhances the absorptivity of mesoporous titania film for a high efficiency dye-sensitized solar cell", *Chemical Communications*, No. 23, issued on 2008, pp. 2635-2637.
"Office Action of Japan Counterpart Application", issued on Dec. 6, 2011, p. 1-p. 4, in which the listed references were cited.

* cited by examiner

*Primary Examiner* — Charanjit Aulakh
(74) *Attorney, Agent, or Firm* — Jianq Chyun IP Office

(57) ABSTRACT

A photosensitizer dye is provided. The photosensitizer dye is a ruthenium (Ru) complex represented by the following general formula (1).

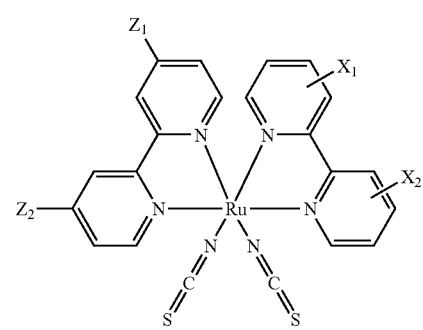

Formula (1)

4 Claims, 1 Drawing Sheet

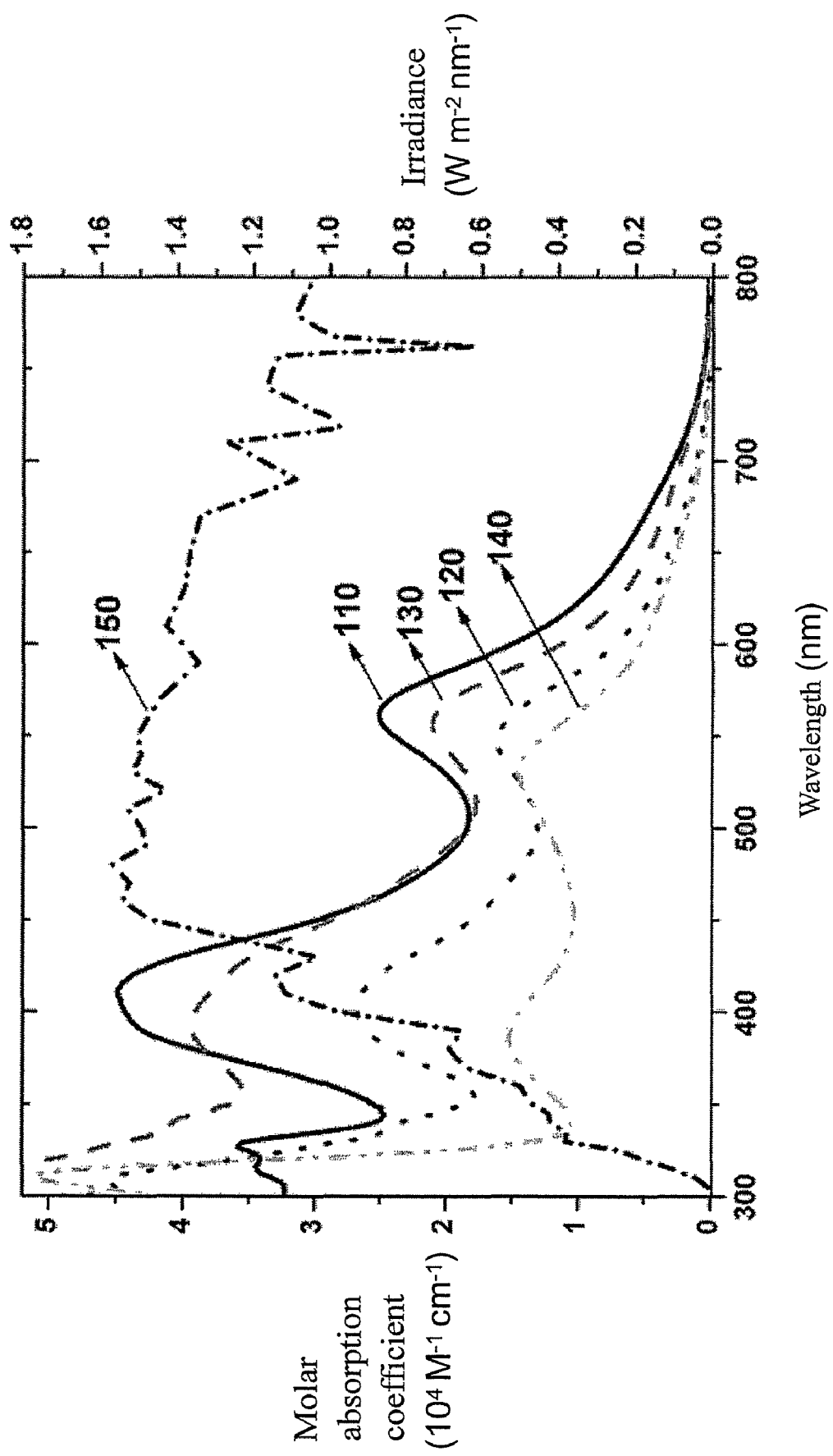

PHOTOSENSITIZER DYE

CROSS-REFERENCE TO RELATED APPLICATION

This application is a continuation-in-part of U.S. application Ser. No. 12/125,939, filed on May 23, 2008, all disclosures is incorporated therewith. The prior application Ser. No. 12/125,939 claims the priority benefit of Taiwan application Serial No. 97105782, filed on Feb. 19, 2008. This application also claims the priority benefit of Taiwan application Serial No. 97148638, filed on Dec. 12, 2008. The entirety of each of the above-mentioned patent applications is hereby incorporated by reference herein and made a part of this specification.

BACKGROUND OF THE INVENTION

1. Field of the Invention

The present invention relates to a solar cell material. More particularly, the present invention relates to a photosensitizer dye applicable in dye-sensitized solar cells (DSCs).

2. Description of Related Art

Not only the supply of fossil fuels is expected to run out in an imminent future, the high consumption of fossil fuels also poses an alarming threat to the environment and public health due to their poisonous emissions. Accordingly, scientists are constantly in searching and developing the renewable and sustainable energy sources. The renewable energy sources include: solar energy, wind energy, hydraulic energy, tidal energy, geothermal energy, biomass energy, and etc. Amongst the various types of energy sources, solar energy has been one of the most pursued due to its abundant supply. Furthermore, the application of solar energy is not limited by the physical environment or geomorphology, and solar energy can be directly converted to electricity with the appropriate devices which are known as solar cells (or photovoltaic cells).

Recently, Grätzel and O'Regan have proposed a new type of solar cell known as dye-sensitized solar cells (DSCs). DSCs offer many advantageous prospects, such as, high photoelectric conversion efficiency, high transparency, colorfulness, and flexibility in which the cell is capable of folding or bending. Hence, the dye-sensitized solar cells are well received in the industry. A dye-sensitized solar cell is typically constituted with four parts including an anode/cathode for current flow, a semiconductor material (such as, titanium dioxide ($TiO_2$) or zinc oxide (ZnO)) for accepting and transporting electrons, a monolayer of photossensitizer (dye) attached onto the surface of the semiconductor material in a self-assembly manner, and an electrolyte for transporting holes. The materials used at each part and the interface between each part in the dye-sensitized solar cell play important roles on the photoelectrical conversion efficiency of the cell. Most particularly, the dye used in the photosensitizer layer is the most critical in determining the efficiency of a dye-sensitized solar cell.

Accordingly, to identify a dye that has a high absorption coefficient for enhancing the photoelectrical conversion efficiency of a dye-sensitized solar cell has been enthusiastically pursued in the dye-sensitized solar cell community.

SUMMARY OF THE INVENTION

In view of the foregoing, the present invention is directed to a photosensitizer dye applied to the dye-sensitized solar cell, wherein the photoelectric conversion efficiency of the dye-sensitized solar cell using this dye is enhanced.

The present invention provides a photosensitizer dye, wherein the photosensitizer dye is a ruthenium (Ru) complex represented by the following general formula (1).

Formula (1)

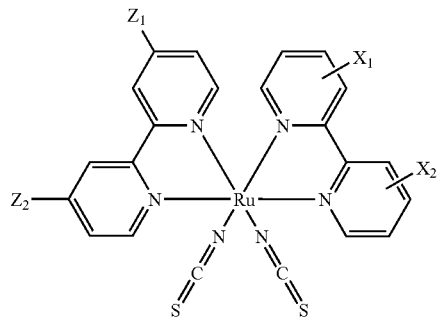

$X_1$ represents one of formula (2) to (19) and $X_2$ represents hydrogen, or $X_1$ and $X_2$ both represent one of formula (2) to (19).

(2)

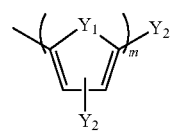

(3)

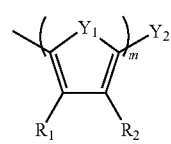

(4)

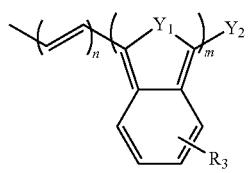

(5)

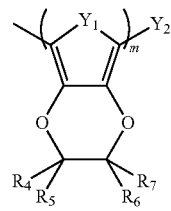

(6)

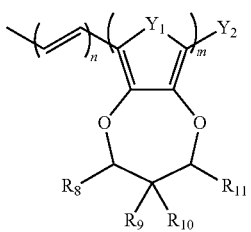

(7)

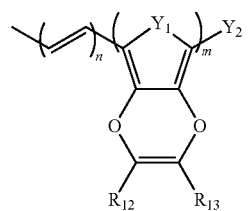

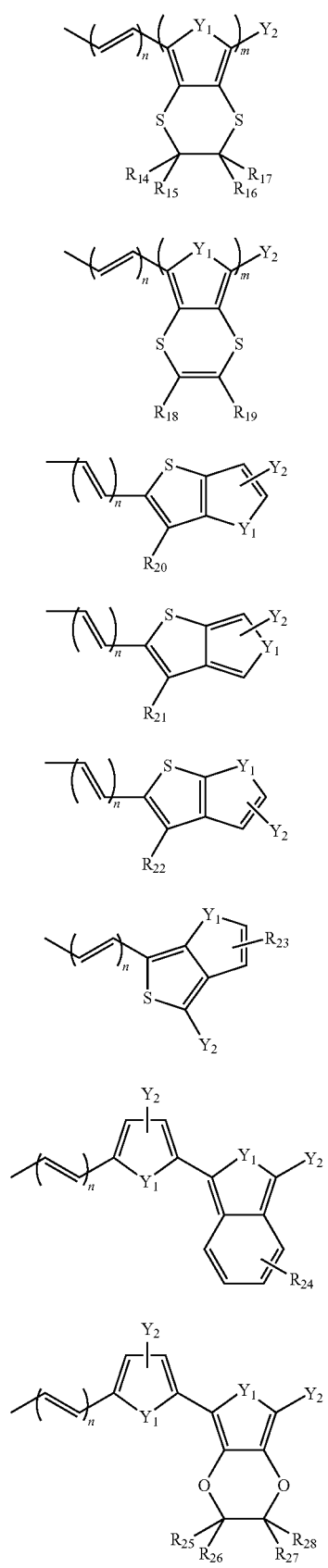
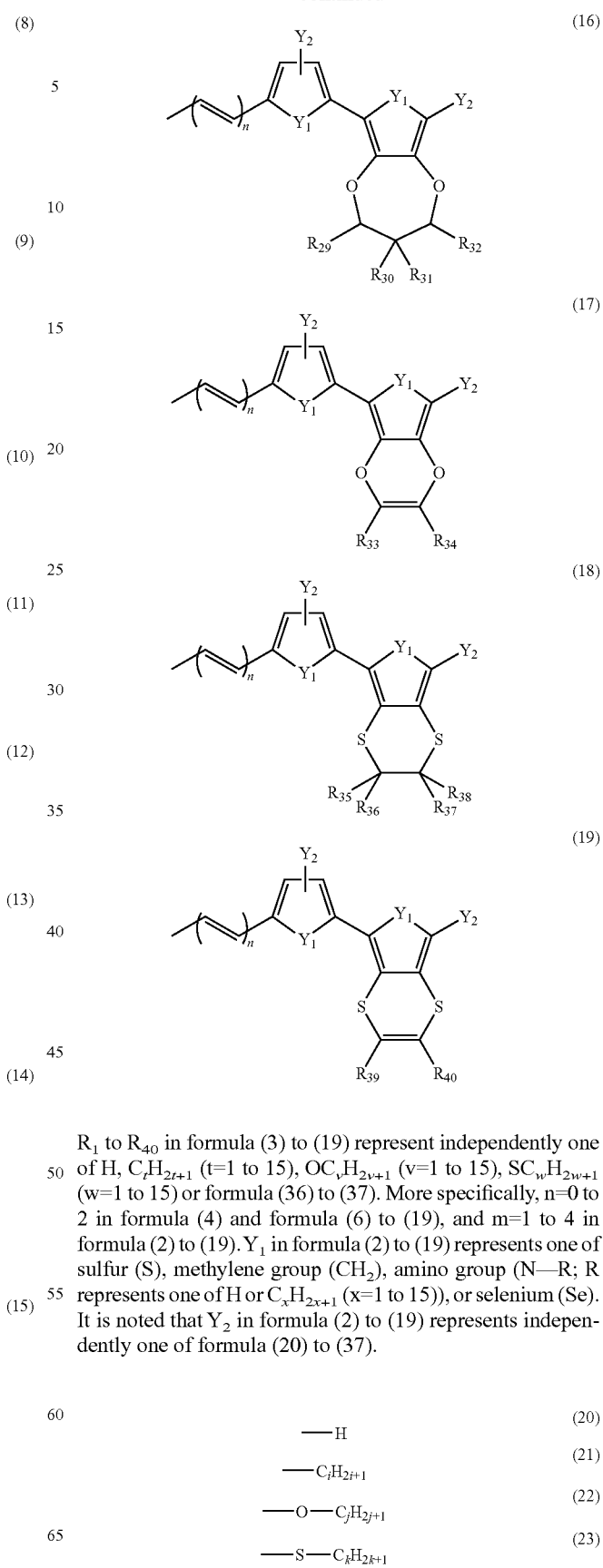

$R_1$ to $R_{40}$ in formula (3) to (19) represent independently one of H, $C_tH_{2t+1}$ (t=1 to 15), $OC_vH_{2v+1}$ (v=1 to 15), $SC_wH_{2w+1}$ (w=1 to 15) or formula (36) to (37). More specifically, n=0 to 2 in formula (4) and formula (6) to (19), and m=1 to 4 in formula (2) to (19). $Y_1$ in formula (2) to (19) represents one of sulfur (S), methylene group ($CH_2$), amino group (N—R; R represents one of H or $C_xH_{2x+1}$ (x=1 to 15)), or selenium (Se). It is noted that $Y_2$ in formula (2) to (19) represents independently one of formula (20) to (37).

-continued
(24) 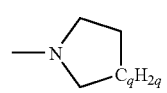
(25) 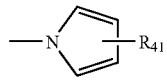
(26) 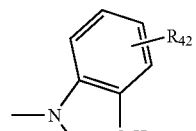
(27) 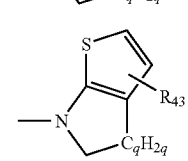
(28) 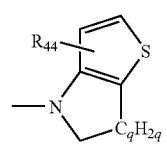
(29) 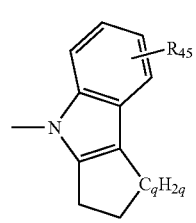
(30) 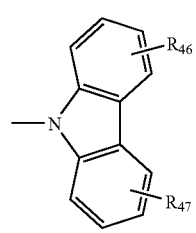
(31) 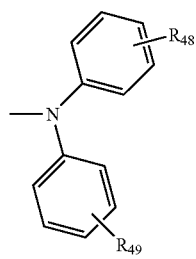
(32) 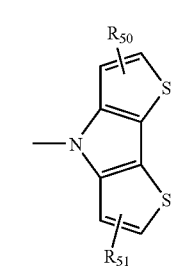
-continued
(33) 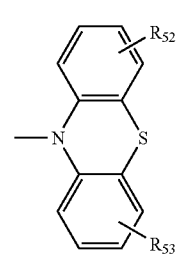
(34) 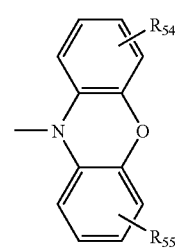
(35) 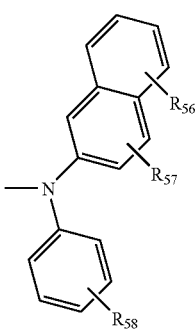
(36) 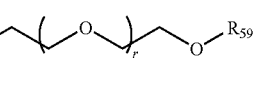
(37) 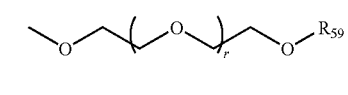
Additionally, in formula (1), $Z_1$ represents one of formula (38) to (44), and $Z_2$ represents hydrogen or one of formula (38) to (44). In other words, $Z_1$ and $Z_2$ can be the identical or different groups.
(38) —COOA$_1$
(39) —PO$_3$HA$_1$
(40) 
(41) 
(42) 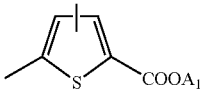

(43)

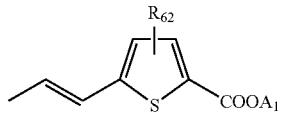

(44)

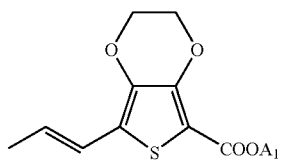

In formula (38) to (44), $A_1$ represents hydrogen (H), lithium (Li), sodium (Na), potassium (K) or tetra-alkyl ammonium groups as represented by general formula (45), or any species or groups with positive charge. Moreover, in formula (45), $R_{63}$, $R_{64}$, $R_{65}$ and $R_{66}$ independently represent H or $C_yH_{2y+1}$ (y=1 to 15).

(45)

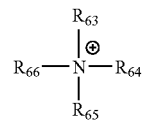

It should be noted that, in formula (1), when $X_2$ represents hydrogen, $Z_1$ and $Z_2$ both represent formula (38) and $X_1$ represents one of formula (2)~(5) in which $Y_1$ represents sulfur (S) and n=0 in formula (4), $Y_2$ in formula (2)~(5) does not represent one of formula (20)~(22).

Besides, in formula (1), when $Z_1$ and $Z_2$ both represent formula (38) and $X_1$ and $X_2$ both represent one of formula (2)~(5) in which $Y_1$ represents sulfur (S) and n=0 in formula (4), $Y_2$ in formula (2)~(5) does not represent one of formula (20)~(22).

In addition, in formula (1), when $Z_1$ and $Z_2$ both represent formula (38) in which $A_1$ represents hydrogen (H) and $X_1$ and $X_2$ both represent formula (10) or formula (12) in which n=0 and $Y_1$ represents sulfur (S), $Y_2$ in formula (10) or formula (12) does not represent one of formula (20)~(23).

According to an embodiment of the present invention, a structure of the photosensitizer dye is represented by the following formula (61) to (67).

(61)

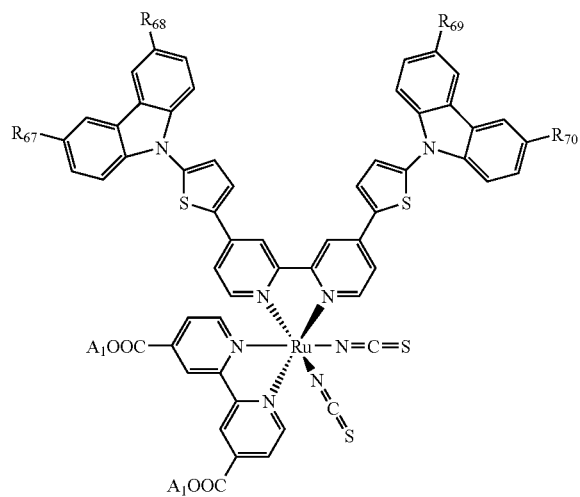

(62)

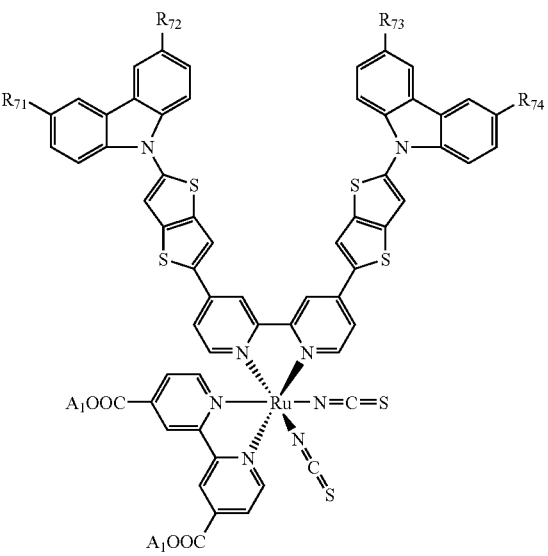

(63)

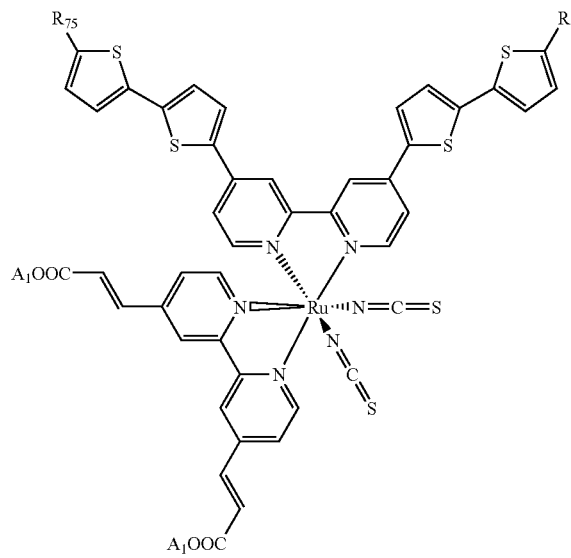

(64)

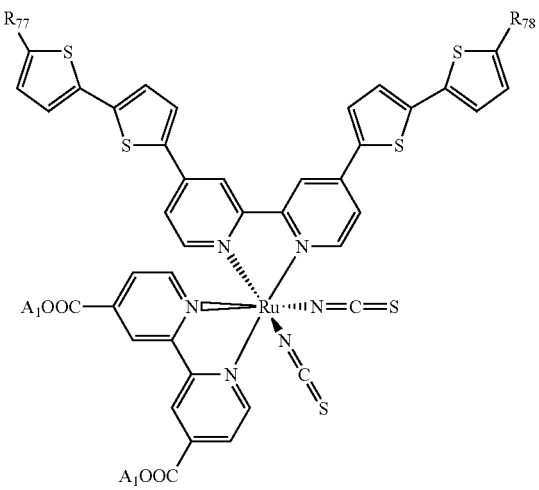

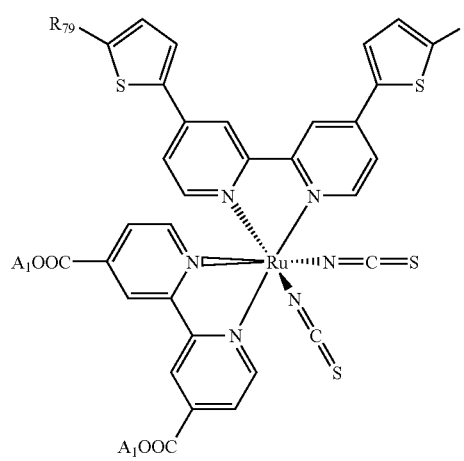

(65)

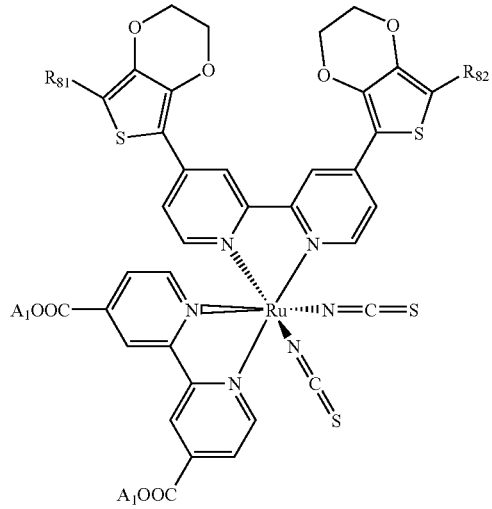

(66)

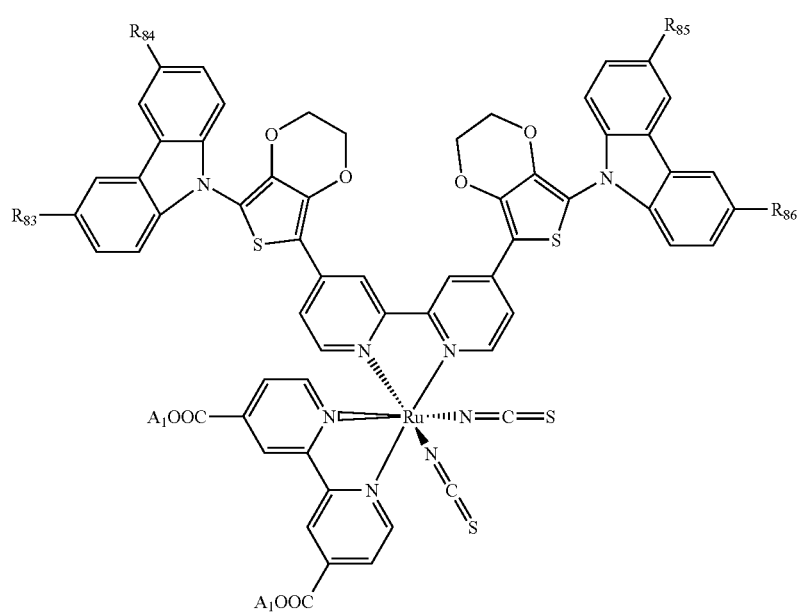

(67)

In formula (61), $R_{67}$, $R_{68}$, $R_{69}$ and $R_{70}$ independently represent one of H, $C_EH_{2E+1}$ (E=1 to 6), $OC_FH_{2F+1}$ (F=1 to 6), $SC_GH_{2G+1}$ (G=1 to 15) or formula (36) to (37). In formula (62), $R_{71}$, $R_{72}$, $R_{73}$ and $R_{74}$ independently represent one of H, $C_AH_{2A+1}$ (A=1 to 15), $OC_BH_{2B+1}$ (B=1~15), $SC_DH_{2D+1}$ (D=1 to 15) or formula (36) to (37). In formula (63), $R_{75}$ and $R_{76}$ independently represent one of H, $C_tH_{2t+1}$ (t=1 to 15), $OC_vH_{2v+1}$ (v=1 to 15), $SC_wH_{2w+1}$ (w=1 to 15) or formula (36) to (37). In formula (64) to (66), $R_{77}$, $R_{78}$, $R_{79}$, $R_{80}$, $R_{81}$, and $R_{82}$ independently represent one of $SC_GH_{2G+1}$ (G=1 to 15) or formula (36) to (37). In formula (67), $R_{83}$, $R_{84}$, $R_{85}$ and $R_{86}$ independently represent one of H, $C_AH_{2A+1}$ (A=1 to 15), $OC_BH_{2B+1}$ (B=1 to 15), $SC_DH_{2D+1}$ (D=1 to 15) or formula (36) to (37). In formula (61) to (67), $A_1$ independently represents hydrogen (H), lithium (Li), sodium (Na), potassium (K) or tetra-alkyl ammonium groups as represented by general formula (45). Moreover, in formula (45), $R_{63}$, $R_{64}$, $R_{65}$ and $R_{66}$ independently represent H or $C_yH_{2y+1}$ (y=1 to 15).

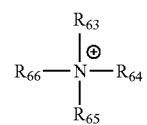

(45)

According to an embodiment of the present invention, a structure of the photosensitizer dye is represented by the following formula (68) to (74).

(68)
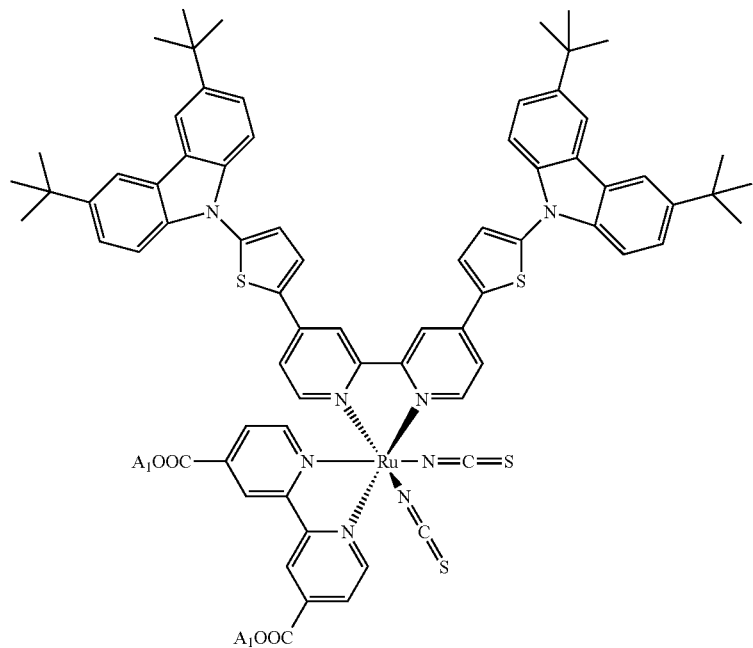
(69)
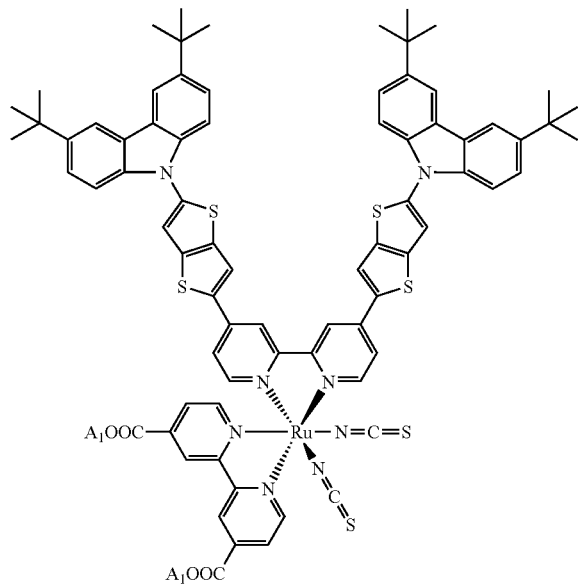
(70)
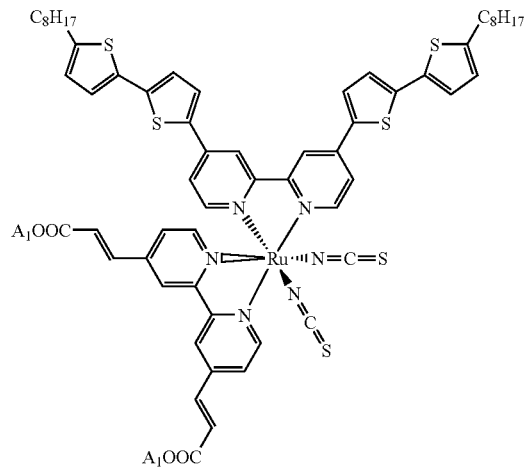

-continued
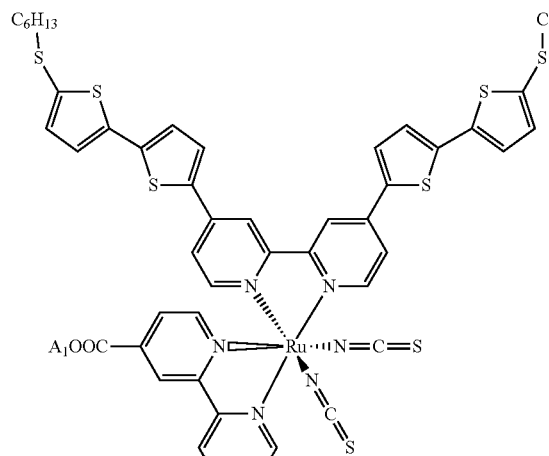
(71)
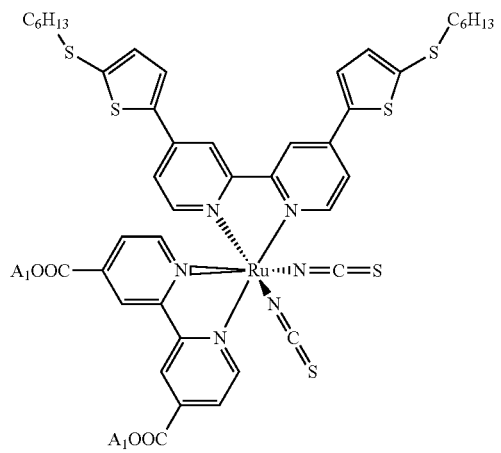
(72)
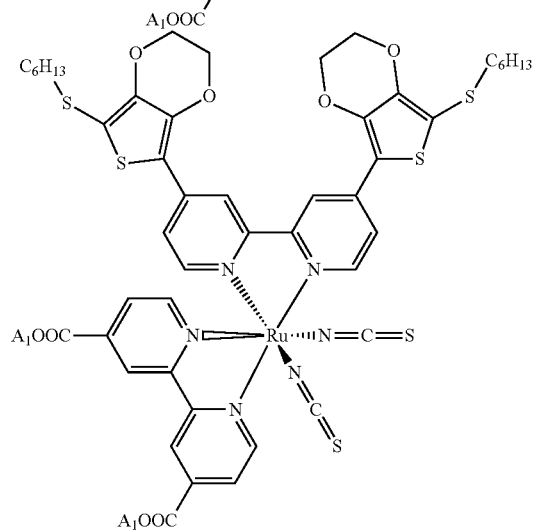
(73)
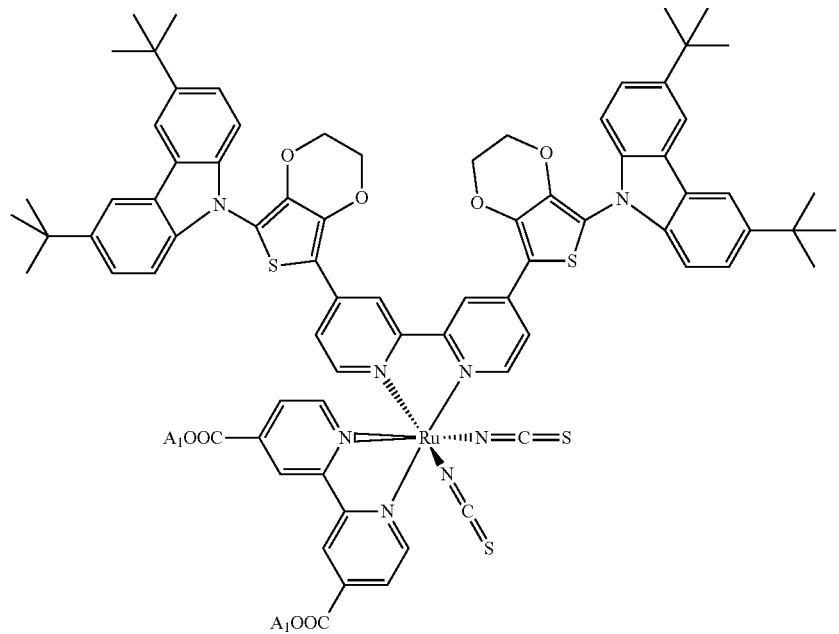
(74)

In formula (68) to (74), $A_1$ independently represents hydrogen (H), lithium (Li), sodium (Na), potassium (K) or tetra-alkyl ammonium groups as represented by general formula (45). As for formula (45), $R_{63}$, $R_{64}$, $R_{65}$ and $R_{66}$ independently represent H or $C_yH_{2y+1}$ (y=1 to 15).

(45)

According to an embodiment of the present invention, a structure of the photosensitizer dye is represented by the following formula (75) to (76).

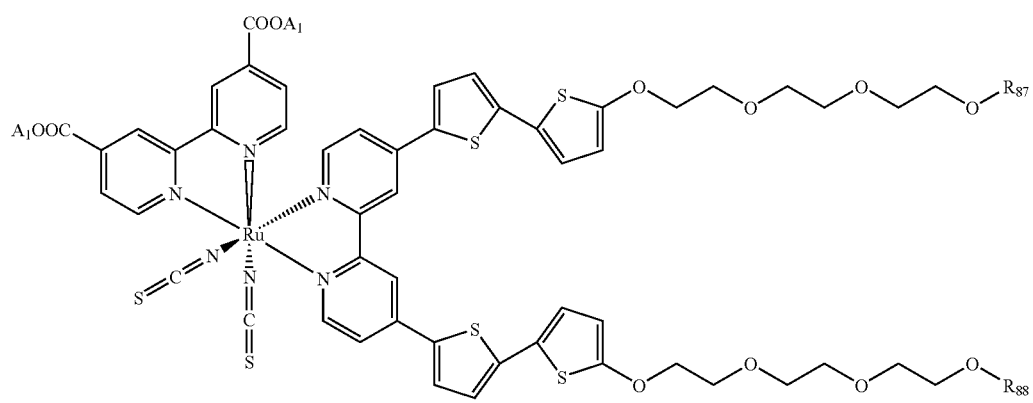

(75)

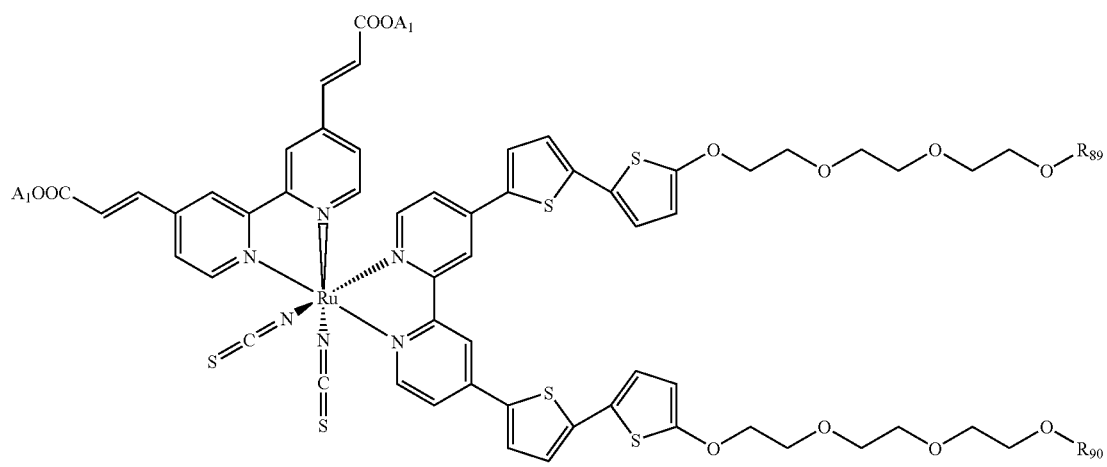

(76)

In formula (75) to (76), $R_{87}$, $R_{88}$, $R_{89}$ and $R_{90}$ independently represent H or $C_jH_{2j+1}$ (J=1 to 15). In formula (75) to (76), $A_1$ independently represents hydrogen (H), lithium (Li), sodium (Na), potassium (K) or tetra-alkyl ammonium groups as represented by general formula (45). $R_{63}$, $R_{64}$, $R_{65}$ and $R_{66}$ of formula (45) independently represent H or $C_yH_{2y+1}$ (y=1 to 15).

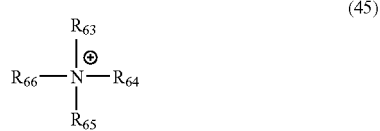

(45)

As mentioned above, the photosensitizer dye in the present invention contains the foregoing special groups ($X_1$, $X_2$, $Z_1$ and $Z_2$). The photosensitizer dye of the present invention has a desirable light absorption capability. In other words, the absorption spectrum of the photosensitizer dye of the present invention is close to the solar light spectrum. Moreover, the absorption coefficient of the photosensitizer dye of the present invention is very high, which suggests that dye-sensitized solar cell using the photosensitizer dye of the present invention can effectively absorb solar light and convert it into an output current.

In order to make the aforementioned items, other features, and advantages of the present invention more comprehensible, preferred embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 1 depicts, in an absorption spectrum, the comparisons between the photosensitizer dyes according to embodiments of the present invention and a conventional photosensitizer dye.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

The present invention provides a photosensitizer dye, wherein the photosensitizer dyes is a ruthenium (Ru) complex represented by the following general formula (1).

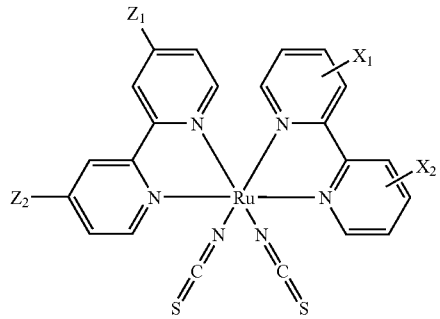

Formula (1)

In formula (1), $X_1$ represents one of formula (2) to (19) and $X_2$ represents hydrogen or, in the alternative, $X_1$ and $X_2$ both represent one of formula (2) to (19).

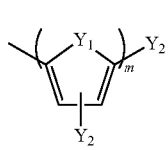

(2)

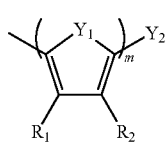

(3)

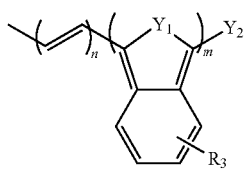

(4)

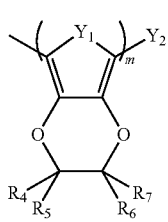

(5)

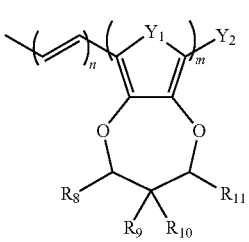

(6)

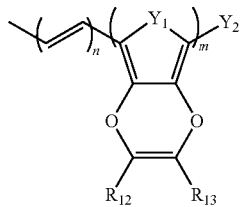

(7)

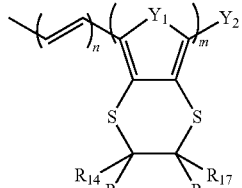

(8)

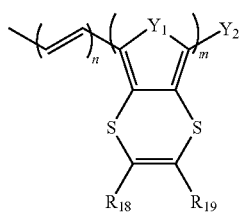

(9)

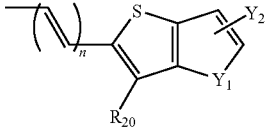

(10)

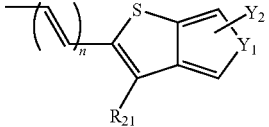

(11)

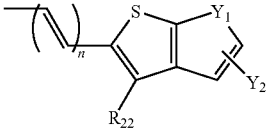

(12)

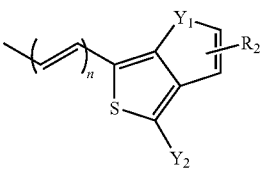

(13)

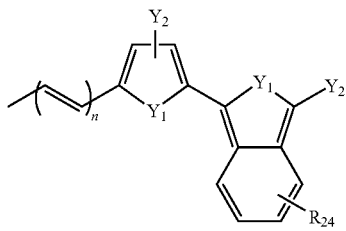

(14)

-continued

(15) 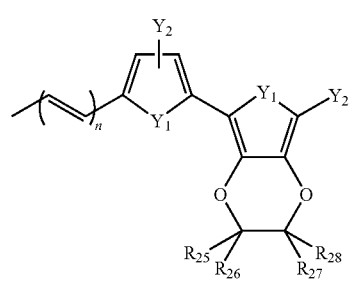

(16) 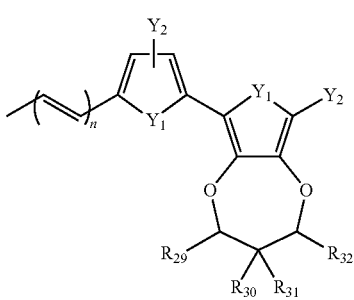

(17) 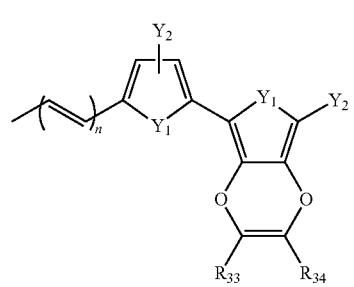

(18) 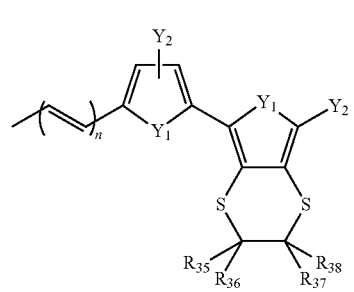

(19) 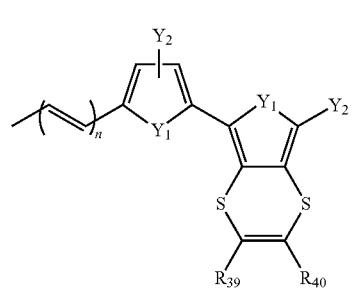

(20) —H

(21) —$C_iH_{2i+1}$

(22) 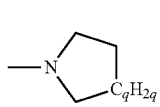

(23) 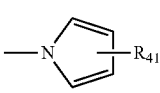

(24) 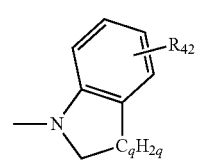

(25) 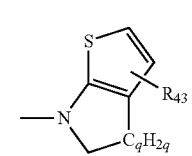

(26) 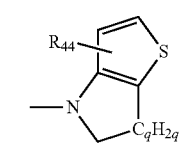

(27) 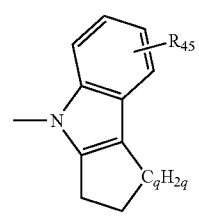

(28) 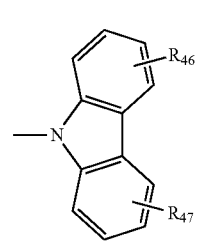

(29) 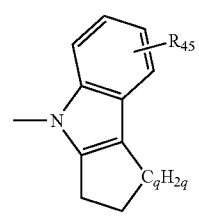

(30) 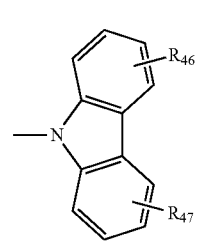

(31) 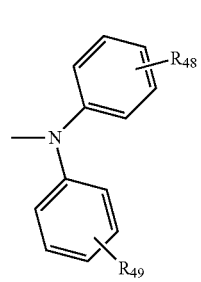

In formula (3) to (19), $R_1$ to $R_{40}$ represent independently one of H, $C_tH_{2t+1}$ (t=1 to 15), $OC_vH_{2v+1}$ (v=1 to 15), $SC_wH_{2w+1}$ (w=1 to 15) or formula (36) to (37). Moreover, n=0 to 2 in formula (4) and formula (6) to (19), and m=1 to 4 in formula (2) to (19). In formula (2) to (19), $Y_1$ represents one of sulfur (S), methylene group ($CH_2$), amino group (N—R; R represents one of H or $C_xH_{2x+1}$ (x=1 to 15)), or selenium (Se). $Y_2$ in formula (2) to (19) represents independently one of formula (20) to (37).

Additionally, in formula (1), $Z_1$ represents one of formula (38) to (44), and $Z_2$ represents hydrogen or one of formula (38) to (44). In other words, $Z_1$ and $Z_2$ can be the identical or different groups.

In formula (38) to (44), $A_1$ represents hydrogen (H), lithium (Li), sodium (Na), potassium (K) or tetra-alkyl ammonium groups as represented by general formula (45), or any species or groups with positive charge. Moreover, in formula (45), $R_{63}$, $R_{64}$, $R_{65}$ and $R_{66}$ independently represent H or $C_yH_{2y+1}$ (y=1 to 15).

It is worthy to note that, in formula (1), when $X_2$ represents hydrogen, $Z_1$ and $Z_2$ both represent formula (38) and $X_1$ represents one of formula (2)~(5) in which $Y_1$ represents sulfur (S) and n=0 in formula (4), $Y_2$ in formula (2)~(5) does not represent one of formula (20)~(22). Furthermore, in formula (1), when $Z_1$ and $Z_2$ both represent formula (38) and $X_1$ and $X_2$ both represent one of formula (2)~(5) in which $Y_1$ represents sulfur (S) and n=0 in formula (4), $Y_2$ in formula (2)~(5) does not represent one of formula (20)~(22). In addition, in formula (1), when $Z_1$ and $Z_2$ both represent formula (38) in which $A_1$ represents hydrogen (H) and $X_1$ and $X_2$ both represent formula (10) or formula (12) in which n=0 and $Y_1$ represents sulfur (S), $Y_2$ in formula (10) or formula (12) does not represent one of formula (20)~(23).

More particularly, in formula (1), when $Z_1$ and $Z_2$ both represent formula (38), $X_1$ represents formula (2) in which $Y_1$ represents sulfur (S) and $X_2$ represents hydrogen or a group the same as $X_1$ (formula (2)), the photosensitizer dye of the present invention is represented as formula (46) and (47), which means $Y_2$ does not represent one of formula (20)~(22) or formula (31). That is to say, $Y_2$ in formula (2) merely represents one of formula (23)~(30) or one of formula (32)~(37).

(46)

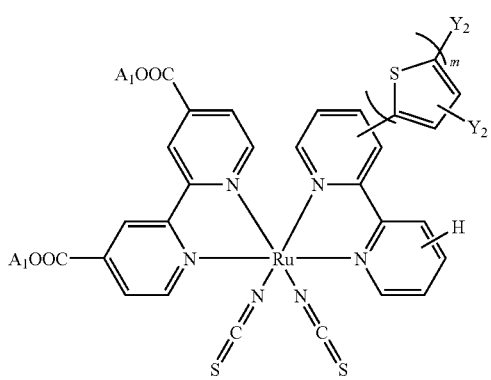

(47)

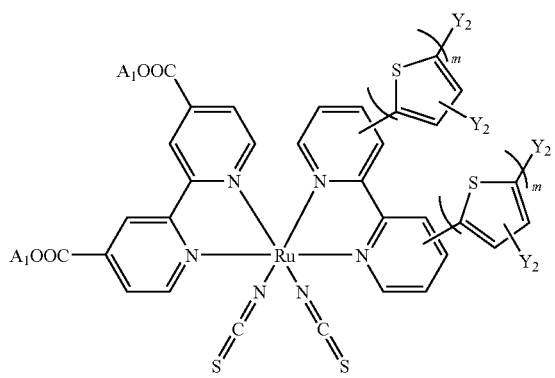

In formula (1), when $Z_1$ and $Z_2$ both represent formula (38), $X_1$ represents formula (3) in which $Y_1$ represents sulfur (S) and $X_2$ represents hydrogen or a group the same as $X_1$ (formula (3)), the photosensitizer dye of the present invention is represented as formula (48) and (49). $Y_2$ in formula (48) to (49) does not represent one of formula (20)~(22) or formula (31). That is to say, $Y_2$ in formula (48) to (49) merely represents one of formula (23)~(30) or one of formula (32)~(37).

(48)

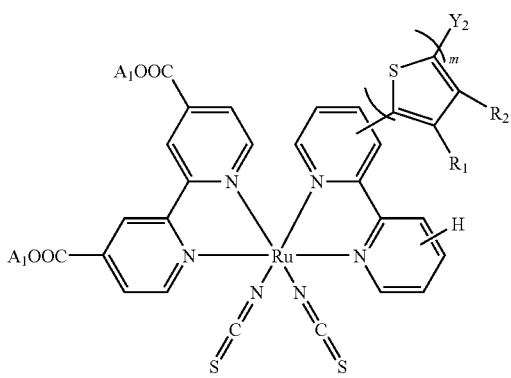

(49)

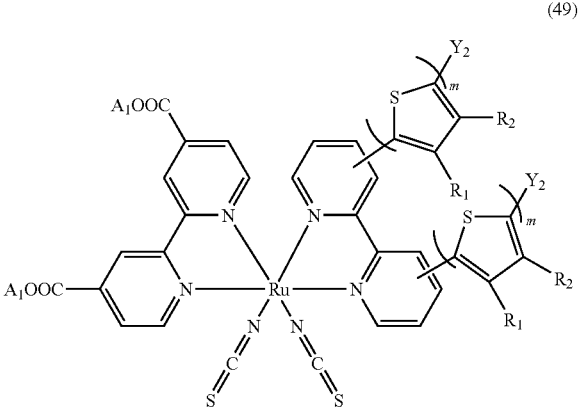

In formula (1), when $Z_1$ and $Z_2$ both represent formula (38), $X_1$ represents formula (4) in which n=0, $Y_1$ represents sulfur (S) and $R_3$ represents hydrogen (H) and $X_2$ represents hydrogen or a group the same as $X_1$ (formula (4)), the photosensitizer dye of the present invention is represented as formula (50) and (51). $Y_2$ in formula (50) to (51) does not represent one of formula (20)~(22). That is to say, $Y_2$ in formula (50) to (51) merely represents one of formula (23)~(37).

(50)

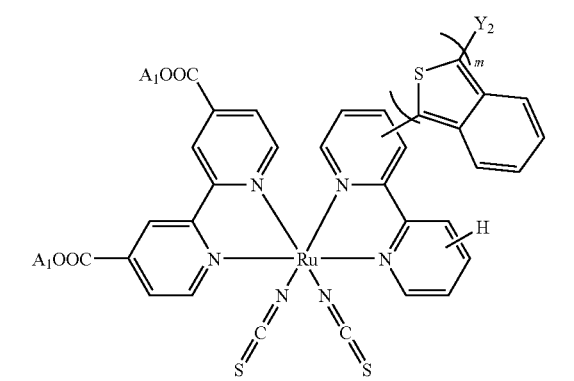

(51)

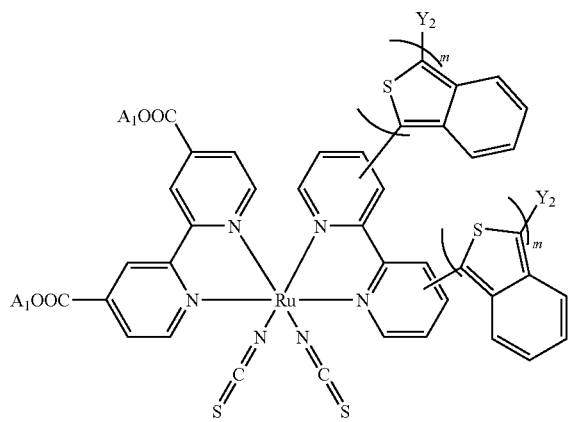

In formula (1), when $Z_1$ and $Z_2$ both represent formula (38), $X_1$ represents formula (5) in which $Y_1$ represents sulfur (S) and $R_4$~$R_7$ represent hydrogen (H) and $X_2$ represents hydrogen or a group the same as $X_1$ (formula (5)), the photosensitizer dye of the present invention is represented as formula

(52) and (53). $Y_2$ in formula (52) and (53) does not represent one of formula (20)~(22). That is to say, $Y_2$ in formula (52) and (53) merely represents one of formula (23)~(37).

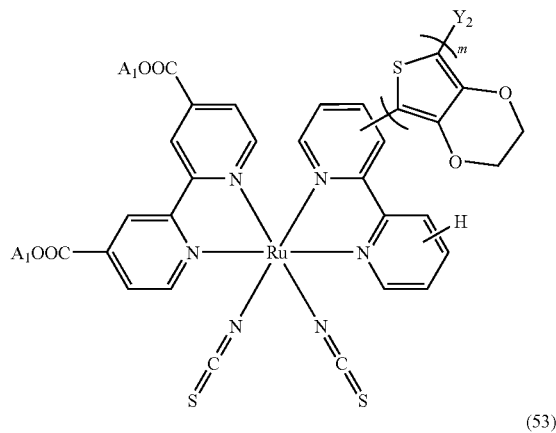

(52)

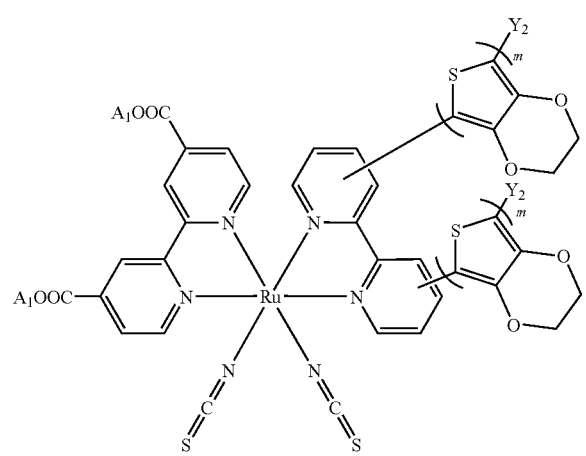

(53)

According to the present invention, the photosensitizer dye contains the above functional groups, that is, $X_1$, $X_2$, $Z_1$ and $Z_2$. Hence, the photosensitizer dye is provided with a desirable light absorption capability. In other words, the absorption spectrum of the photosensitizer dye of the present invention is close to the solar light spectrum, and the absorption coefficient of the photosensitizer dye of the present invention is pretty high.

In general, the potential energy level of the excited state, i.e. lowest unoccupied molecular orbital (LUMO), of the photosensitizer dye has to match the potential energy level of the conduction band of the metal oxide (for example, titanium dioxide or zinc oxide, etc.) used in the dye-sensitized solar cells. Accordingly, electrons can be effectively transported from the photosensitizer dye to the metal oxide, and energy loss during the transfer process is minimized.

Additionally, the oxidation potential, i.e. energy level of the highest occupied molecular orbital (HOMO), of the photosensitizer dye has to be slightly lower than the redox potential of the electrolytes (such as, iodine ions) or other materials having hole-transporting property. Accordingly, the photosensitizer dye, after losing an electron, can effectively retrieve an electron from the electrolytes or other hole-transporting materials.

Since the photosensitizer dye of the present invention contains the above special groups ($X_1$, $X_2$, $Z_1$ and $Z_2$), the energy level of the HOMO and LUMO of the photosensitizer dye is compatible well with the oxidation potential of the electrolyte and the conduction band of the anode in a dye-sensitized solar cell (DSC). As a result, the dye-sensitized solar cells (DSCs) using the above-mentioned photosensitizer dye has higher photoelectric conversion efficiency.

In the following embodiments, some of the chemical structures in the foregoing ruthenium (Ru) complexes having a desirable light absorption capability will be introduced.

In an embodiment of the present invention, a structure of the photosensitizer dye is represented by the following formula (61) to (67).

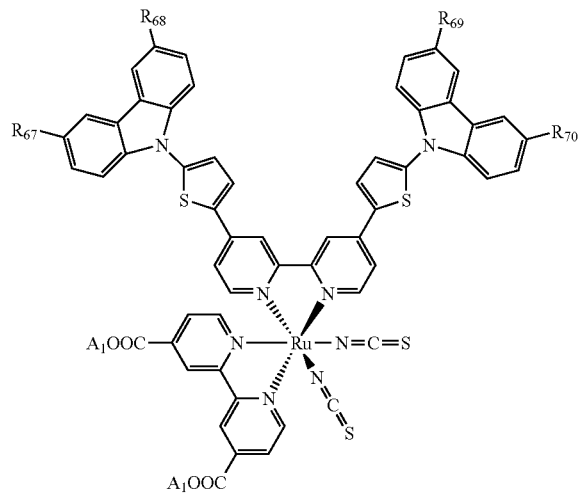

(61)

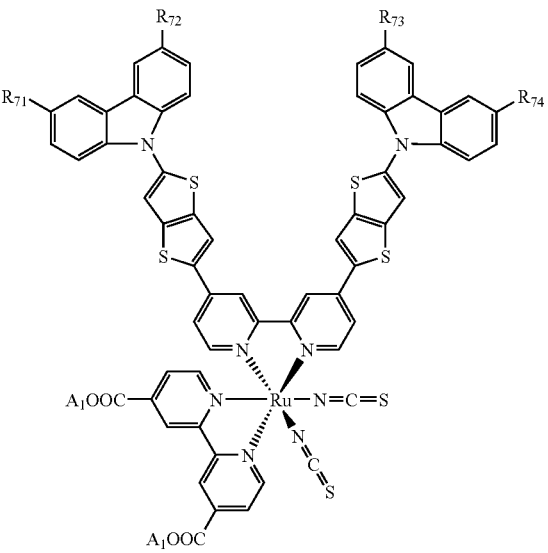

(62)

-continued
(63)
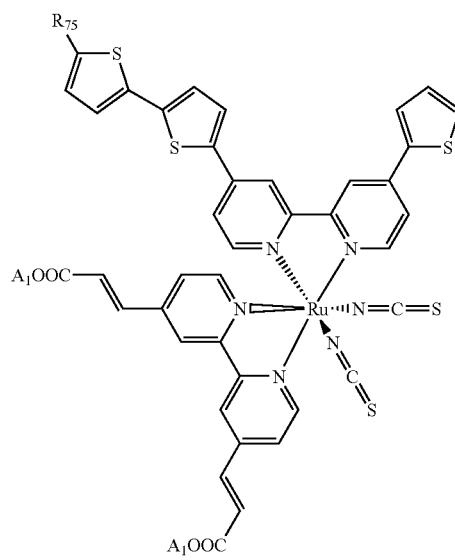
(64)
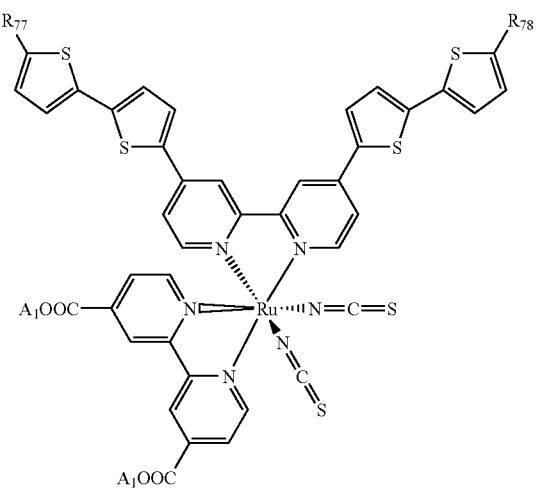
(65)
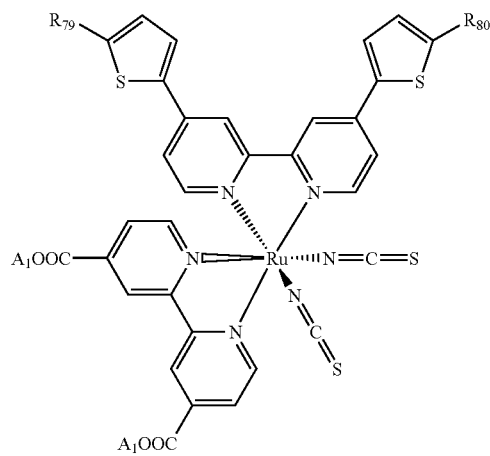
(66)
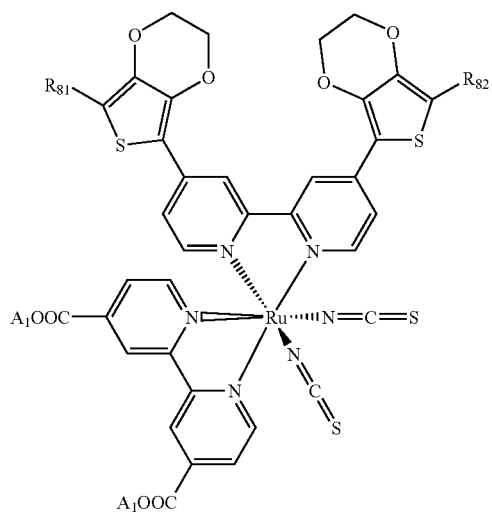
(67)
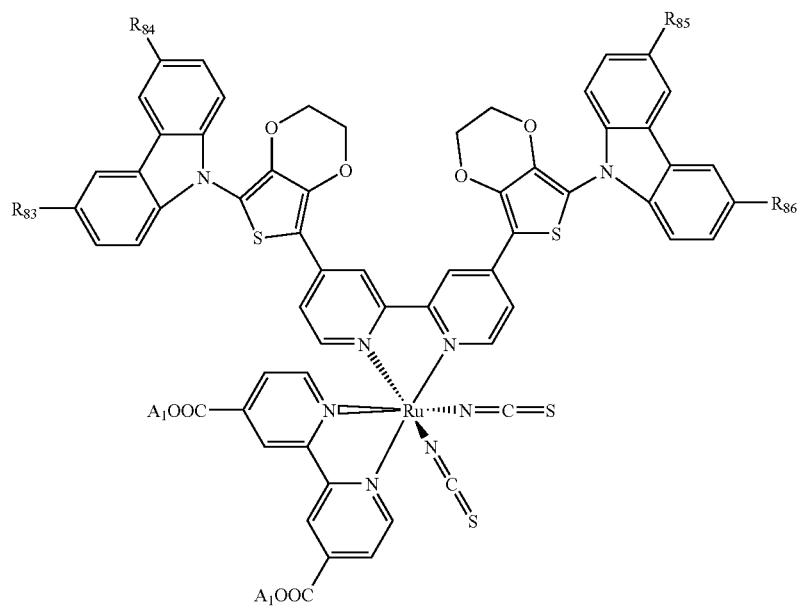

In formula (61), $R_{67}$, $R_{68}$, $R_{69}$ and $R_{70}$ independently represent one of H, $C_EH_{2E+1}$ (E=1 to 6), $OC_FH_{2F+1}$ (F=1 to 6), $SC_GH_{2G+1}$ (G=1 to 15) or formula (36) to (37). In formula (62), $R_{71}$, $R_{72}$, $R_{73}$ and $R_{74}$ independently represent one of H, $C_AH_{2A+1}$ (A=1 to 15), $OC_BH_{2B+1}$ (B=1 to 15), $SC_DH_{2D+1}$ (D=1 to 15) or formula (36) to (37). In formula (63), $R_{75}$ and $R_{76}$ independently represent one of H, $C_tH_{2t+1}$ (t=1 to 15), $OC_vH_{2v+1}$ (v=1 to 15), $SC_wH_{2w+1}$ (w=1 to 15) or formula (36) to (37). In formula (64) to (66), $R_{77}$, $R_{78}$, $R_{79}$, $R_{80}$, $R_{81}$ and $R_{82}$ independently represent one of $SC_GH_{2G+1}$ (G=1 to 15) or formula (36) to (37). In formula (67), $R_{83}$, $R_{84}$, $R_{85}$ and $R_{86}$ independently represent one of H, $C_AH_{2A+1}$ (A=1 to 15), $OC_BH_{2B+1}$ (B=1 to 15), $SC_DH_{2D+1}$ (D=1 to 15) or formula (36) to (37). In formula (61) to (67), $A_1$ independently represents hydrogen (H), lithium (Li), sodium (Na), potassium (K) or tetra-alkyl ammonium groups as represented by general formula (45). Moreover, in formula (45), $R_{63}$, $R_{64}$, $R_{65}$ and $R_{66}$ independently represent H or $C_yH_{2y+1}$ (y=1 to 15).

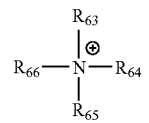

(45)

In an embodiment of the present invention, a structure of the photosensitizer dye is represented by the following formula (68) to (74).

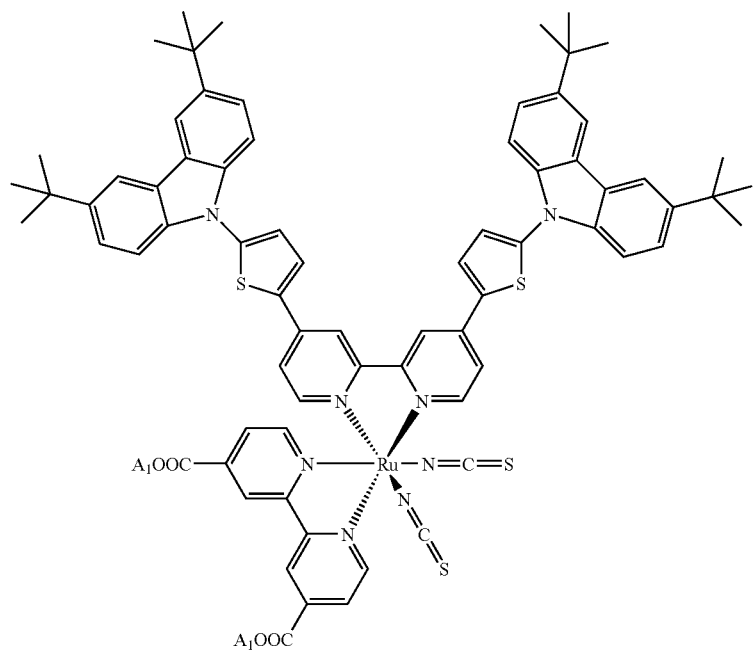

(68)

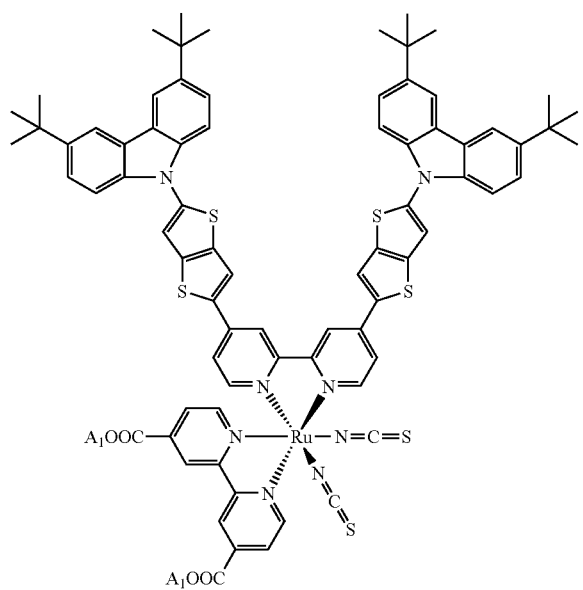

(69)

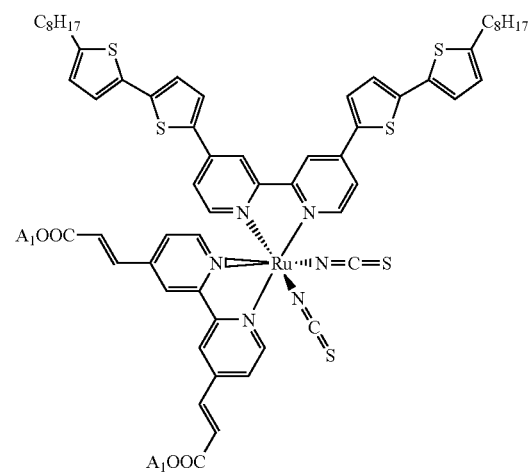

(70)

-continued
(71)
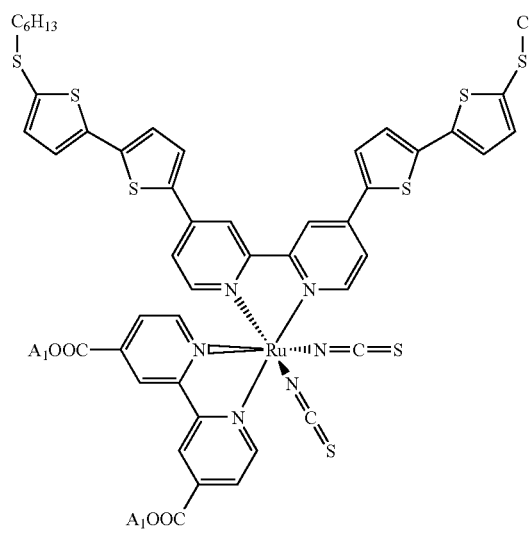
(72)
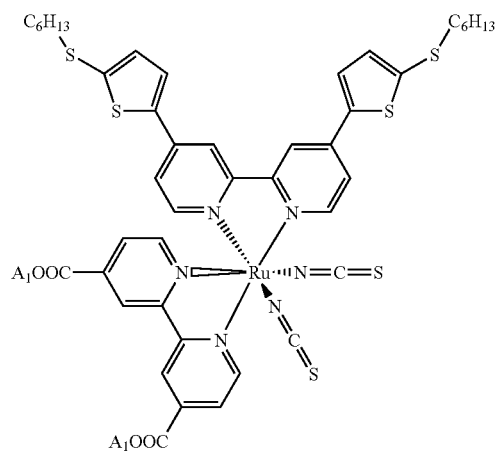
(73)
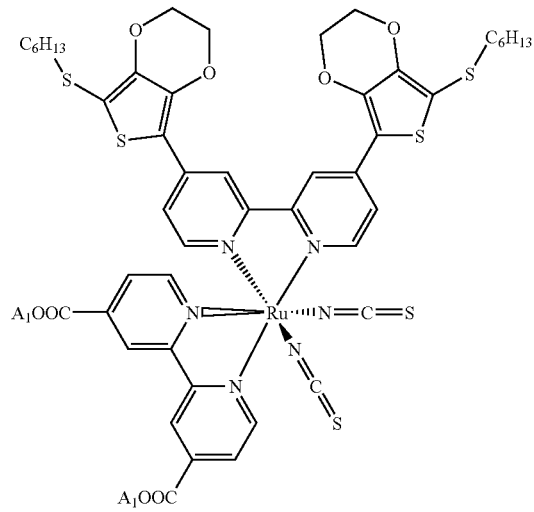
(74)
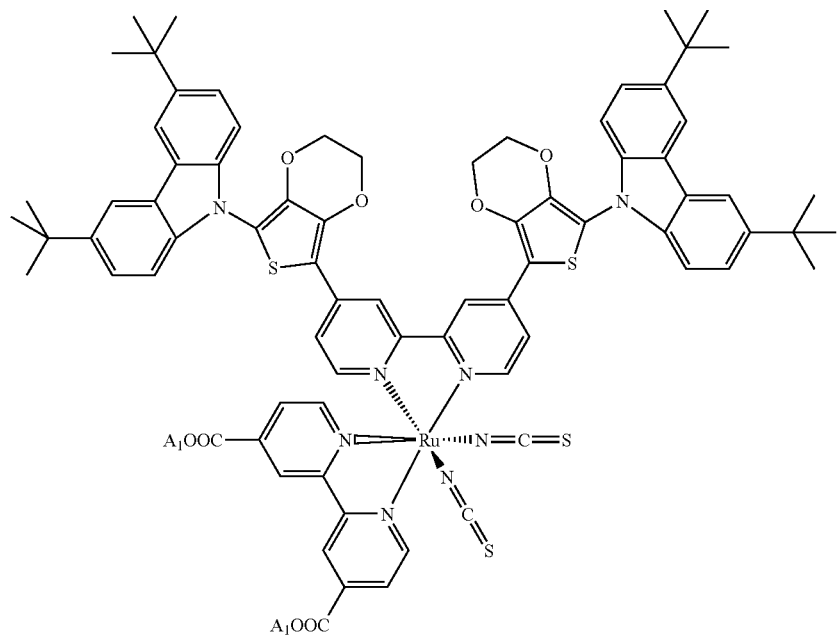

In formula (68) to (74), $A_1$ independently represents hydrogen (H), lithium (Li), sodium (Na), potassium (K) or tetra-alkyl ammonium groups as represented by general formula (45). As for formula (45), $R_{63}$, $R_{64}$, $R_{65}$ and $R_{66}$ independently represent H or $C_yH_{2y+1}$ (y=1 to 15).

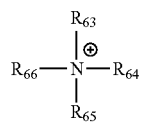

(45)

In an embodiment of the present invention, a structure of the photosensitizer dye is represented by the following formula (75) to (76).

In formula (75) to (76), $R_{87}$, $R_{88}$, $R_{89}$ and $R_{90}$ independently represent H or $C_JH_{2J+1}$ (J=1 to 15). In formula (75) to (76), $A_1$ independently represents hydrogen (H), lithium (Li), sodium (Na), potassium (K) or tetra-alkyl ammonium groups as represented by general formula (45). $R_{63}$, $R_{64}$, $R_{65}$ and $R_{66}$ of formula (45) independently represent H or $C_yH_{2y+1}$ (y=1 to 15).

The following disclosure describes the synthesis of three ruthenium (Ru) complex dyes of the present invention, and also an analysis of the experimental data regarding to the light absorption capability of these ruthenium (Ru) complexes. It should be appreciated that the following description is provided for illustration purposes, and is not construed to limit the scope of the present invention.

The First Synthesis Example

The chemical compound (represented as CYC-B5 hereinafter) is used as an example to illustrate the synthesis of a ruthenium (Ru) photosensitizer dye according to the first synthesis example of the present invention.

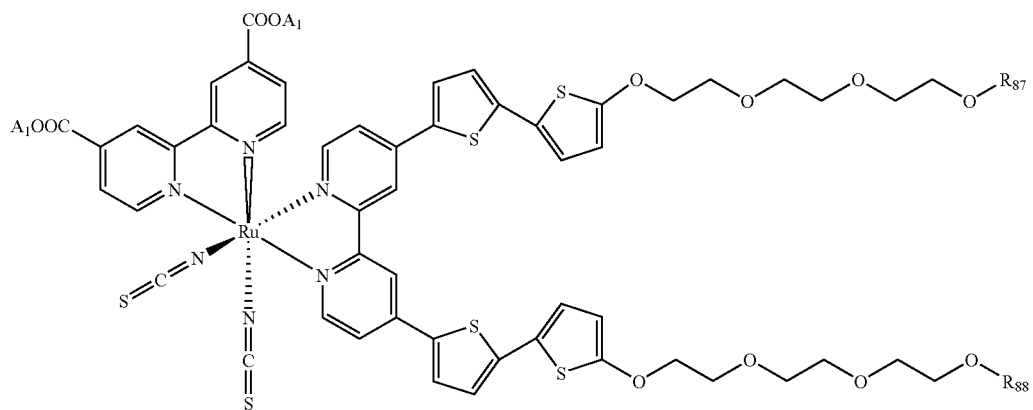

(75)

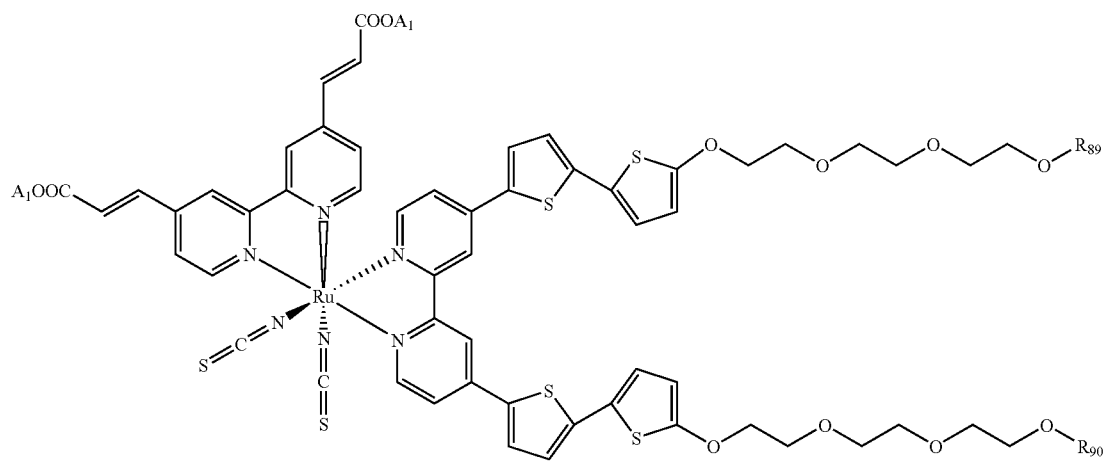

(76)

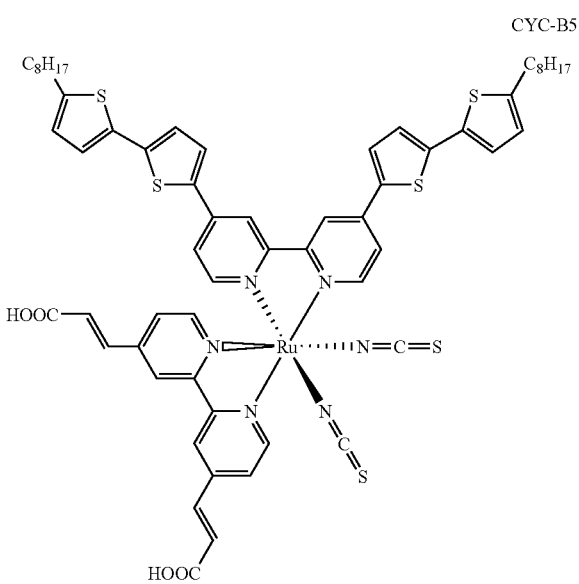

CYC-B5

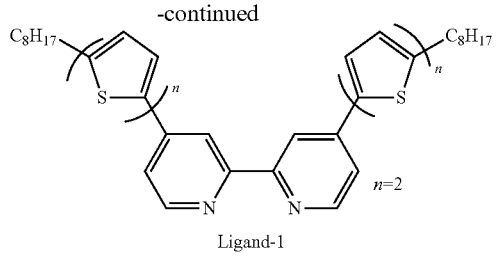

Ligand-1

CYC-B5 is a compound with a structure of formula (1) when $X_1$ and $X_2$ in formula (1) are the same group and $X_1$ represents the above formula (3), $Y_1$ in formula (3) represents sulfur (S), m=2, $R_1$ and $R_2$ both represent hydrogen (H), $Y_2$ represents formula (21), and $C_iH_{2i+1}$ in formula (21) is $C_8H_{17}$. Wherein $Z_1$ and $Z_2$ are the same group and $Z_1$ represents the group of formula (40), and $A_1$ represents hydrogen (H).

The processes in synthesizing an ancillary ligand (represented as Ligand-1), which is 4,4'-bis(5-octyl-2,2'-bithiophen-5-yl)-2,2'-bipyridine), of CYC-B5 is presented as the following:

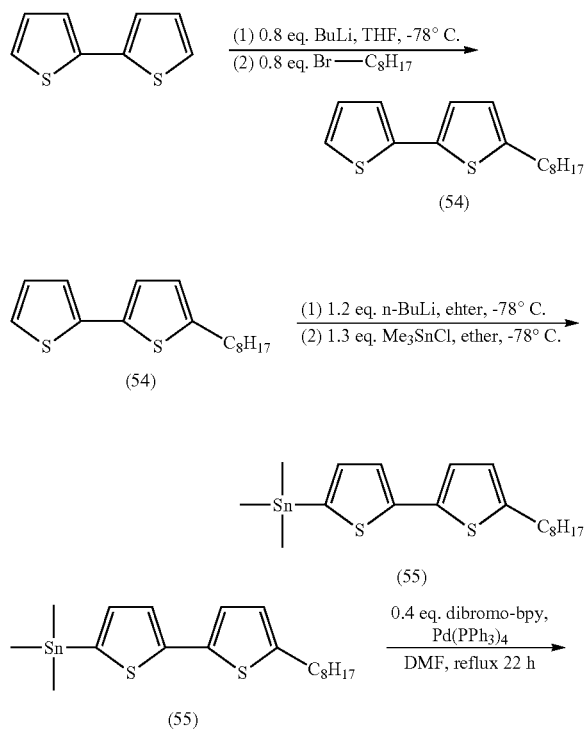

wherein THF represents tetrahydrofuran ($C_4H_8O$), DMF represents dimethylformamide ($C_3H_7NO$), and ether is ethyl ether ($C_4H_{10}O$).

The process is commenced by placing about 4 g of bithiophene in a round-bottom flask with a side arm, followed by adding an anhydrous THF solvent to dissolve the bithiophene. The temperature of the resulting solution is then lowered to −78° C. (for example, using liquid nitrogen plus ethanol as a cryogen). Thereafter, about 7.6 ml of n-butyl lithium (n-BuLi) (2.5 M, dissolved in hexane) is gradually drop-added into the bithiophene solution. After the temperature of the resulting solution has returned to the room temperature, the solution is continuously stirred for about 15 minutes.

The process is then continued by adding 4.6 ml of 1-bromooctane (Br—$C_8H_{17}$) to the solution, and the solution is continuously stirred for about 10 hours. After a predetermined period of reaction time, deionized water is added to terminate the reaction, and then the product is extracted with ether. An organic layer is collected, and the impurity in the organic layer is extracted by using respectively a saturated sodium hydrogen carbonate aqueous solution, deionized water and a saturated sodium chloride aqueous solution. The resulting crude product is purified using column chromatography (using hexane as an eluent) to obtain 5.4 g of an intermediate product. The intermediate product is 5-octyl-2,2'-bithiophene ($C_{16}H_{22}S_2$), which is represented by formula (54). The yield is about 80.5%.

Thereafter, about 4.2 g of 5-octyl-2,2'-bithiophene is dissolved in anhydrous THF. The temperature of the solution is lowered to −78° C. using a cryogen, followed by gradually drop-adding 6.0 ml of n-BuLi (2.5M, dissolved in hexane) to the solution. After this, the temperature of the solution is returned to room temperature, and the solution is stirred for about two hours. Then, the temperature of the solution is again lowered to −78° C., and about 3.16 g of chlorotrimethyl stannane ($C_3H_9ClSn$) (dissolved in an appropriate amount of THF) is added to the solution.

After the temperature of the solution is returned to room temperature, the solution is continuously stirred for about 12 hours. Thereafter, deionized water is added to terminate the reaction, and an extraction is performed using respectively a saturated sodium hydrogen carbonate aqueous solution, deionized water and a saturated sodium chloride solution. An organic layer is then collected, and the solvent is removed to obtain about 6.0 g of the crude product, which is trimethyl (5-octyl-2,2'-bithiophene)stannane ($C_{19}H_{30}S_2Sn$) and represented by formula (55).

Thereafter, about 6.0 g of 8-(trimethyltin)-2-octylbithiophene and about 2.0 g of 4-4'-dibromo-2,2'-bipyridine (the method for synthesizing this compound can be referred to I. Murase, Nippon Kagaku Zasshi, 1956, 77, 682; G. Mnerker and F. H. Case, J. Am. Chem. Soc., 1958, 80, 2745; and D. Wenkert and R. B. Woodward, J. Org. Chem., 1983, 48, 283) are dissolved in 60 ml of anhydrous dimethylformamide (DMF). About 0.44 g of tetrakis(triphenylphosphine) palladium [Pd(PPh$_3$)$_4$] is added as a catalyst. After this, the solution is heated and refluxed for about 22 hours. When the temperature of the solution returns to room temperature, about 5 wt % of ammonium chloride aqueous solution is added to terminate the reaction.

After this, an extraction is performed using dichloromethane, and an organic layer is collected. Extraction of the organic layer is conducted using respectively a sodium hydrogen carbonate aqueous solution, deionized water and a saturated sodium chloride aqueous solution. After removing the solvent of the organic layer, a crude product is obtained. The crude product is purified by column chromatography (using hexane as an eluent), and the remaining solid substance is further extracted with ethyl acetate using a Soxhlet extractor to obtain 5.0 of the first ligand (represented as Ligand-1). The yield is about 47.0%.

The process in synthesizing a ruthenium (Ru)-containing photosensitizer dye (CYC-B5) is as follows.

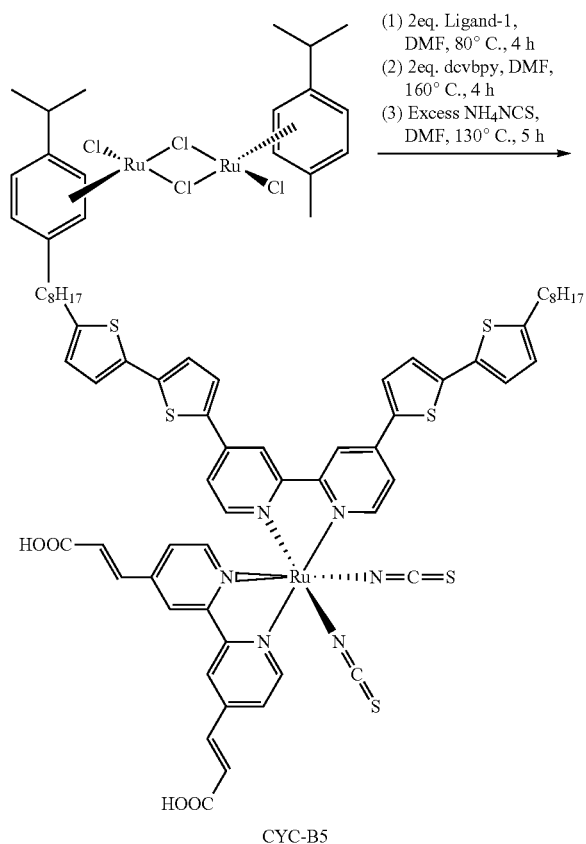

CYC-B5

After Ligand-1 was prepared, 0.4323 g of [RuCl$_2$(p-cymene)]$_2$ and 1.0 g of Ligand-1 are dissolved in 30 ml of the anhydrous DMF. The solution is then heated to about 80° C. for about 4 hours. After this, about 0.4183 g of 4,4'-bis(E-carboxyvinyl)-2,2'-bi-pyridine (dcvbpy; the synthesis method can be referred to Klein et al., Inorg. Chem., 2005, 44, 178) is added to the solution, followed by heating the solution to about 160° C. for 4 hours. It is worthy to note that the above reaction must be conducted in the dark to prevent the generation of isomers.

Then, an excessive amount of NH$_4$NCS is added to the solution, and the reaction is allowed to continue for about 5 hours at a temperature about 130° C. After the reaction completed, the temperature of the solution is returned to room temperature. The solution is concentrated by removing the solvent DMF using a vacuum system, followed by a washing process using respectively deionized water, sodium hydroxide solution at pH 12 and ethyl ether to obtain a solid substance. A crude product is ultimately obtained after vacuum filtration.

After dissolving the crude product in methanol and passing the solution through a column (using methanol as an eluent), a dark color portion is collected and methanol is removed by rotary evaporation. The resulting black solid substance is purified using ethyl acetate to remove the soluble impurities. Then, acetone is used as a solvent to remove the impurities that are dissolvable in acetone. The black solid substance, after being sequentially washed with ethyl acetate and acetone, is dissolved in a mixture solution of methanol and tetra-butyl ammonium hydroxide aqueous solution. The resulting solution then passes through a column (using Sephadex LH-20 as a packing material), and a darker color portion of the solution is collected. Few drops of a 0.01 M nitric acid aqueous solution are added to the solution for adjusting the pH to 3, and a precipitation of about 0.69 g is obtained. The precipitation is the product (CYC-B5), and the yield of CYC-B5 is about 40.0%.

Structural analysis and evaluation of the product (CYC-B5) are discussed as follows.

Mass spectrometry (LRMS (FAB)) analysis: theoretical value: m/z −1222.2 ([M]$^+$); experimental value: m/z −1222.2 (m) ([M]$^+$). HRMS (FAB): experimental value: m/z −1222.2004. Elemental analysis of CYC-B5 (C$_{60}$H$_{60}$N$_6$O$_4$S$_6$Ru): theoretical value: C, 58.94; H, 4.95; N, 6.87%; experimental values: C, 58.82; H, 5.79. N, 6.43%. $^1$H-NMR spectrum signal (500 MHz, $\delta_H$/ppm in d$_6$-DMSO, J Hz): 9.26 (H); 9.15 (2 protons); 9.05 (H); 8.99 (H); 8.91 (H); 8.22 (2 protons); 8.15 (H); 8.02 (H); 7.80 (H); 7.73 (H); 7.55 (H); 7.51 (H); 7.48 (2 protons); 7.39 (2 protons); 7.34 (H); 7.25 (H); 7.21 (H); 6.98 (H); 6.90 (H); 6.84 (H); 2.81 (2H); 2.78 (2H); 1.65 (2H); 1.62 (2H); 1.26 (20H); 0.85 (6H) ○

The Second Synthesis Example

The second synthesis example is used to illustrate the synthesis of a chemical compound according to another embodiment of invention. This compound is represented as CYC-B6S.

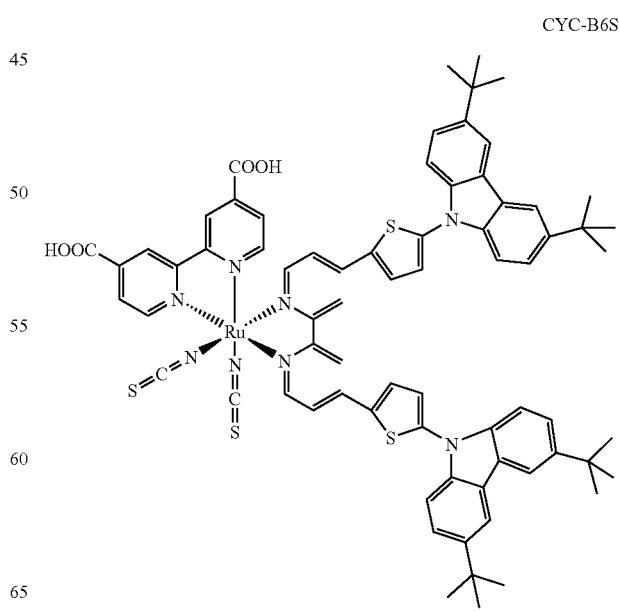

CYC-B6S

CYC-B6S is a compound with a structure of formula (1) when $X_1$ and $X_2$ in formula (1) are the same group, and $X_1$ represents the group of formula (3), and $Y_1$ of formula (3) represents sulfur (S), m=1, $R_1$ and $R_2$ both represent hydrogen (H), and $Y_2$ represents formula (30). $R_{46}$ and $R_{47}$ in formula (30) both represent $C_4H_9$. Wherein $Z_1$ and $Z_2$ are the same group and $Z_1$ represents the group of formula (38), and $A_1$ represents hydrogen (H).

The process flow in synthesizing the ancillary ligand (represented as Ligand-6S) of CYC-B6S is presented as follows:

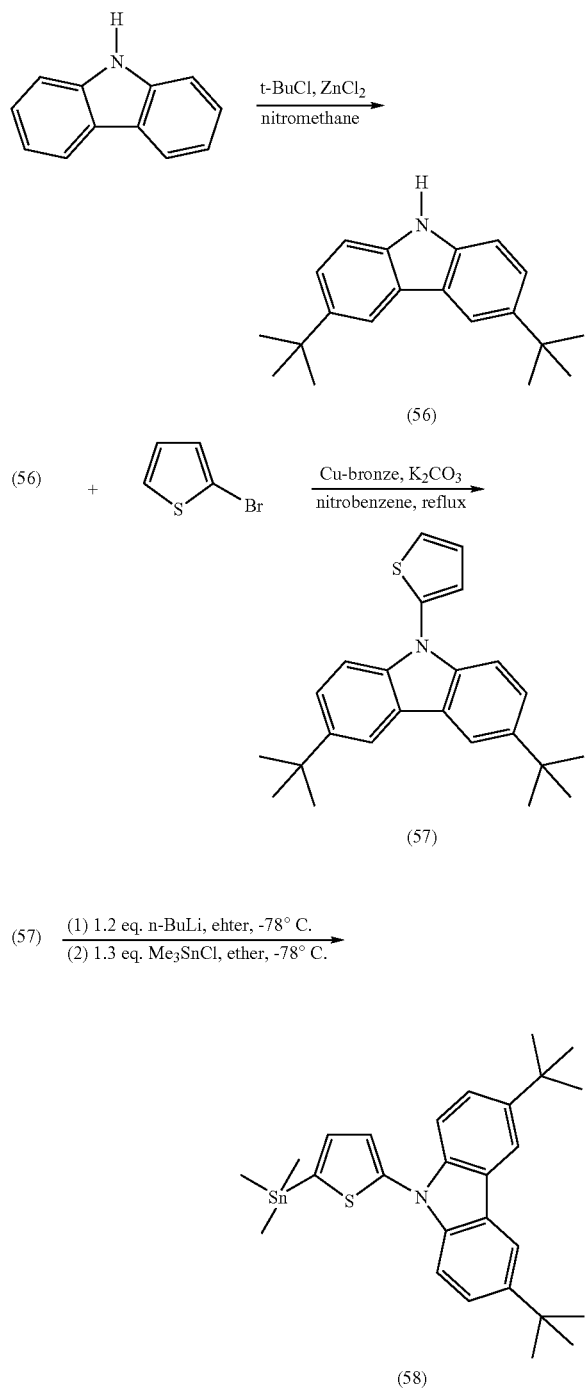

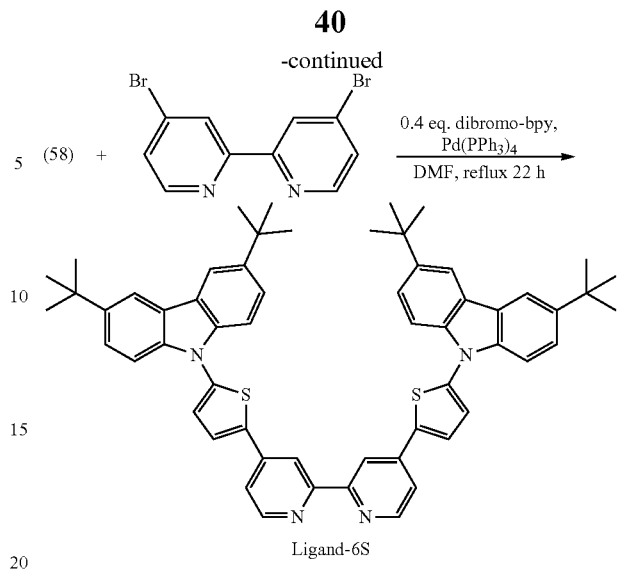

wherein nitromethane represents $CH_3NO_2$, nitrobenzene represents $C_6H_5NO_2$, THF represents tetrahydrofuran, DMF represents dimethylformamide, ether represents ethyl ether.

The process is commenced by placing about 10 g of carbazole ($C_{12}H_9N$) in a round-bottom flask with a side arm, followed by adding 300 ml of nitromethane and 25 g of $ZnCl_2$. Then, 20 ml of tert-butyl chloride (t-BuCl) is gradually drop-added to the solution and the solution is continuously stirred at room temperature for about 20 hours. The resulting solution is transferred to a beaker, and 350 ml of water is added to the beaker for performing a hydrolysis reaction.

After a predetermined period of reaction time, dichloromethane ($CH_2Cl_2$) is added to perform an extraction, and an organic layer is collected. Extraction of the impurity in the organic layer is carried out using respectively deionized water and a saturated sodium chloride aqueous solution. The resulting crude product is purified using a recrystallization method (the solvent being hexane) to obtain a first intermediate product, 3,6-di-tert-butylcarbazole (represented by formula (56)), in which the yield is about 60.6%.

About 10.13 g of the first intermediate product (represented by formula (56)), 6.6 g of potassium carbonate ($K_2CO_3$), 6.7 g of Cu-bronze and 7.1 g of 2-bromo-thiopene ($C_4H_3B_4S$) are placed in a round-bottom flask with a side arm. Nitrobenzene ($C_6H_5NO_2$) is further added to the flask and a reflux reaction is conducted under nitrogen gas for 80 hours. Thereafter, the solvent is removed, and ammonia aqueous solution is added. The resulting solution is continuously stirred for about 2 hours. A large amount of water and $CHCl_3$ are added to perform an extraction, and an organic layer is collected. Then, the water in the organic layer is removed using magnesium sulfate ($MgSO_4$), and a majority of the solvent is removed after filtering and rotary evaporation. After this, further purification is performed using column chromatography to obtain a second intermediate product (represented by formula (57)). Wherein the yield of the second intermediate product is about 57.2%.

Then, 1.48 g of the second intermediate product is placed in a round-bottom flask with a side arm. Approximately 60 ml of anhydrous tetrahydrofuran is added to the flask. The temperature of the round-bottom flask is controlled at about −78° C. (use ethanol and liquid nitrogen to control the temperature). After this, 2.0 ml of n-butyl lithium (n-BuLi) solution (2.5 M, dissolved in hexane) is slowly injected into the flask. After the temperature of the solution has returned to room temperature, the solution is stirred for 2 hours. Afterwards, 1.1 g of $Me_3SnCl$ is slowly injected into the solution, and then the solution is stirred for another 10 hours. A large amount of water and dichloromethane ($CH_2Cl_2$) are added (to dissolve the organic layer) to perform an extraction. After an organic layer (lower layer) is collected, the organic layer is readily washed with saturated NaCl (aq). The solvent in the collected product is removed using a rotary evaporator to obtain 2.1 g of the third intermediate product, as represented by formula (58).

About 2.1 g of the third intermediate product and 2.0 g of 4,4'-dibromo-2,2'-biphyridine (the method of synthesis of this compound can be referred to I. Murase, Nippon Kagaku Zasshi, 1956, 77, 682; G. Mnerker and F. H. Case, J. Am. Chem. Soc., 1958, 80, 2745; and D. Wenkert and R. B. Woodward, J. Org. Chem., 1983, 48, 283) are dissolved in 60 ml of anhydrous dimethylformamide (DMF), and about 0.25 g of tetrakis(triphenylphosphine) palladium is added as a catalyst. The mixture is heated and refluxed for about 22 hours. When the temperature of the mixture returns to room temperature, about 5 wt % of ammonium chloride aqueous solution is added to terminate the reaction. An extraction is performed using dichloromethane, and an organic layer is collected.

Thereafter, another extraction of the organic layer is conducted using respectively a sodium hydrogen carbonate aqueous solution, deionized water and a saturated sodium chloride aqueous solution. When the solvent of the organic layer is removed, a crude product is obtained. The crude product is purified by column chromatography (using hexane as an eluent), and the remaining solid substance is further extracted with a Soxhlet extractor (using ethyl acetate as a solvent) to obtain 1.1 g of product, Ligand-6S. The yield of Ligand-6S is about 71.1%.

The process flow in synthesizing a ruthenium (Ru)-containing photosensitizer dye (CYC-B6S) is described as follows:

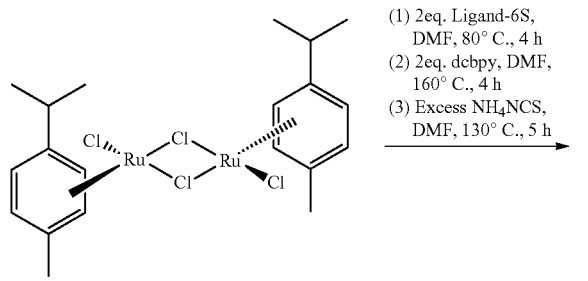

(1) 2eq. Ligand-6S, DMF, 80° C., 4 h
(2) 2eq. dcbpy, DMF, 160° C., 4 h
(3) Excess $NH_4NCS$, DMF, 130° C., 5 h

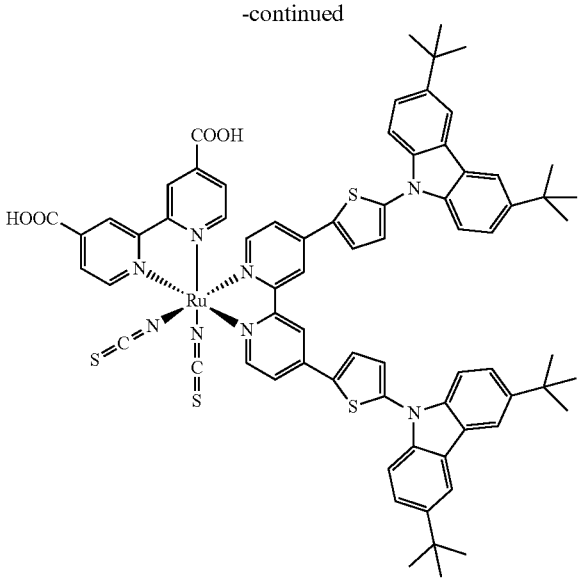

CYC-B6S wherein DMF represents dimethylformamide.

After Ligand-6S was prepared, 0.3848 g of [$RuCl_2$(p-cymene)]$_2$ and 1.1 g of Ligand-6S are dissolved in 80 ml of anhydrous dimethylformamide, and the resulting solution is heated to 80° C. After allowing the reaction to continue for 4 hours, 0.31 g of dcbpy (4,4'-dicarboxylic acid-2,2'-bipyridine) is added. The solution is heated to 160° C. and the reaction is continued for another 4 hours. The subsequent purification procedure of the resulting product is the same as the purification process of CYC-B5, as mentioned above. Thereafter, the product (CYC-B6S) of about 0.68 g in weight is obtained, and the yield of CYC-B6S is about 40.3%.

Structural analysis and evaluation of the product (CYC-B6S) are discussed as follows.

Mass spectrometry analysis (LRMS (FAB)): theoretical value: m/z −1336.3 ([M]$^+$); experimental value: m/z −1336.0 (m) ([M]$^+$). (HRMS (FAB)): experimental value: m/z −1336.3160. Elemental analysis of CYC-B6S ($C_{72}H_{66}N_8O_4S_4Ru$): theoretical value: C, 64.70; H, 4.98; N, 8.38%; experimental value: C, 64.15; H, 6.10; N, 7.83%. $^1$H-NMR spectrum signal (500 MHz, $\delta_H$/ppm in d6-DMSO, J Hz): 9.45 (H); 9.25 (H); 9.17 (H); 9.13 (H); 9.01 (H); 8.97 (H); 8.34~8.29 (6 protons); 8.19 (H); 7.95 (H); 7.67 (2H); 7.62~7.57 (4 protons); 7.55 (H); 7.50 (6 protons); 1.43 (18H); 1.39 (18H).

The Third Synthesis Example

The third synthesis example is used to illustrate the synthesis of a chemical compound according to another embodiment of this invention. This chemical compound is represented as pre-CYC-B12.

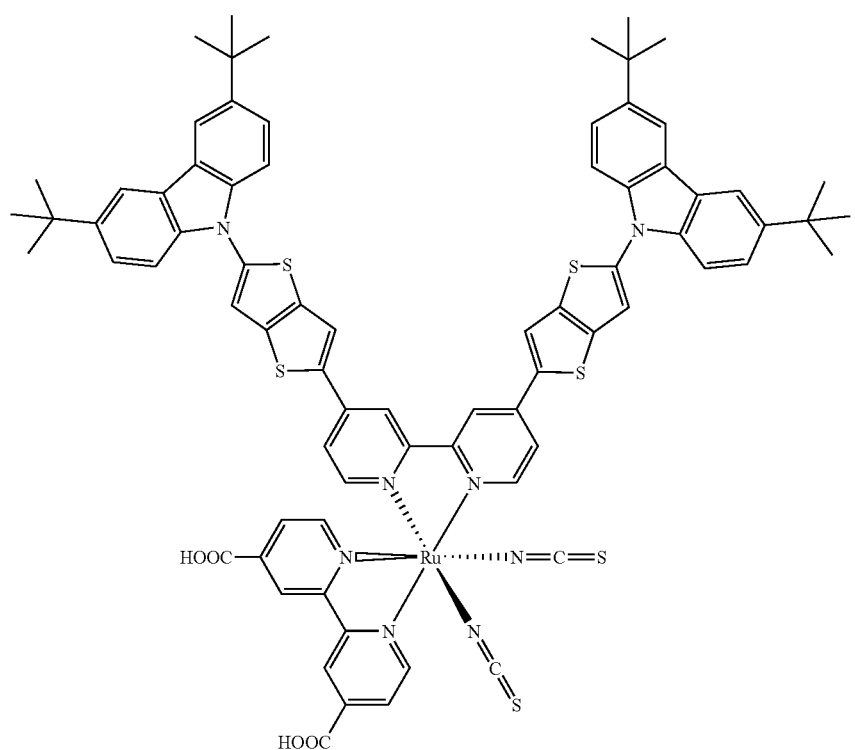

pre-CYC-B12

Pre-CYC-B12 is a compound with a structure of formula (1) when $X_1$ and $X_2$ in formula (1) are the same group, and $X_1$ represents the group of formula (10), n=0, $R_1$ in formula (10) represents hydrogen (H), $Y_1$ represents sulfur (S), and $Y_2$ represents formula (30). $R_{46}$ and $R_{47}$ in formula (30) both represent $C_4H_9$. Wherein $Z_1$ and $Z_2$ are the same group and $Z_1$ represents the group of formula (38), and $A_1$ represents hydrogen (H).

The process flow in synthesizing an ancillary ligand (represented as Ligand-12), which is 4,4'-bis(3,6-di-tert-butyl-carbazol-9-yl-thieno[3,2-b]thiophen-5-yl)-2,2'-bipyridine, is presented in the following.

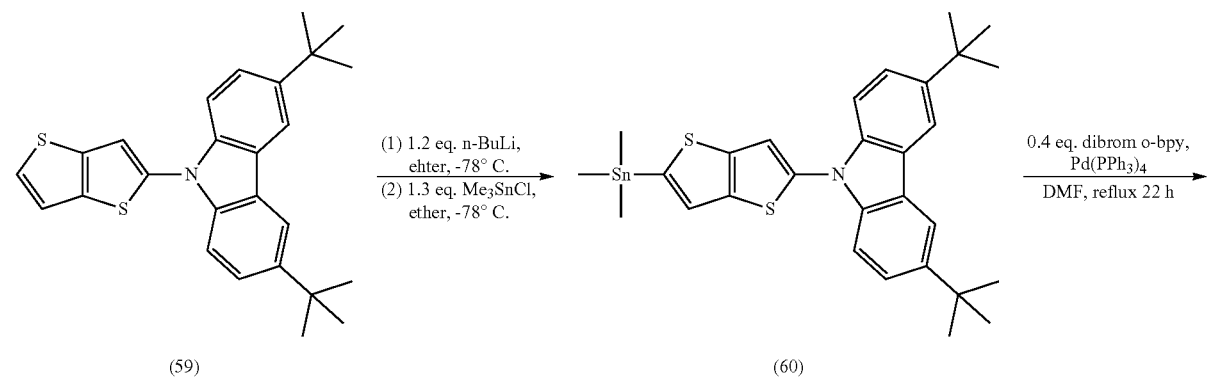

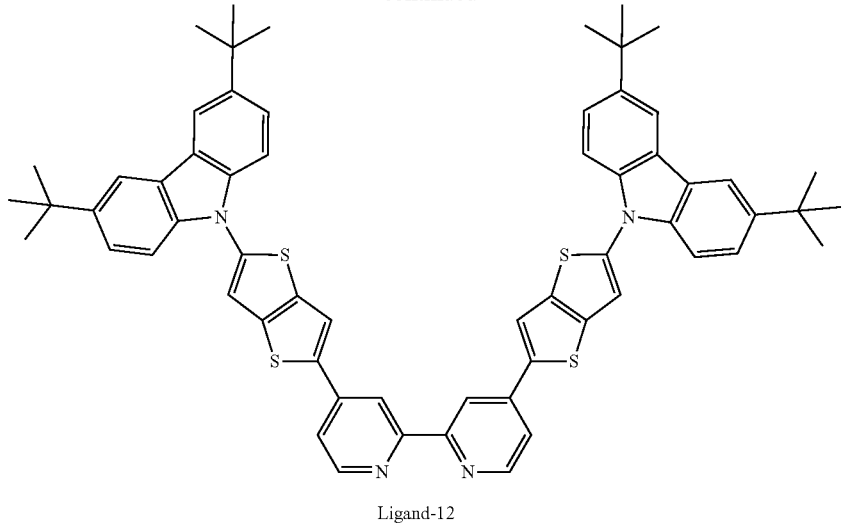

Ligand-12

The process is commenced by placing 5.11 g of a reactant (represented by formula (59)) in a round-bottom flask with a side arm, followed by adding approximately 65 ml of anhydrous tetrahydrofuran. The temperature of the round-bottom flask is controlled at about −78° C. (may use ethanol and liquid nitrogen to control the temperature). After this, 5.9 ml of n-butyl lithium (n-BuLi) solution (2.5 M, dissolved in hexane) is slowly injected into the flask. After the temperature of the solution has returned to room temperature, the solution is stirred for 2 hours. Subsequently, 3.3 g of $Me_3SnCl$ is slowly injected into the solution, and then the solution is stirred for another 10 hours. A large amount of water and chloroform ($CHCl_3$) are added (to dissolve the organic layer) to perform an extraction. After an organic layer (lower layer) is collected, the organic layer is readily washed with saturated NaCl (aq). The solvent in the collected product is removed using a rotary evaporator to obtain 7.0 g of the intermediate product, as represented by formula (60).

About 7.0 g of the intermediate product (formula (60)) and 1.7 g of 4,4'-dibromo-2,2'-biphyridine (the method for synthesizing this compound can be referred to I. Murase, *Nippon Kagaku Zasshi*, 1956, 77, 682; G. Mnerker and F. H. Case, *J. Am. Chem. Soc.*, 1958, 80, 2745; and D. Wenkert and R. B. Woodward, *J. Org. Chem.*, 1983, 48, 283) are dissolved in 150 ml of anhydrous dimethylformamide (DMF), and about 0.76 g of tetrakis(triphenylphosphine) palladium is added as a catalyst. The mixture is heated and refluxed for about 22 hours. When the temperature of the mixture returns to room temperature, about 5 wt % of ammonium chloride aqueous solution is added to terminate the reaction. An extraction is performed using chloroform, and an organic layer is collected. Thereafter, another extraction of the organic layer is conducted using respectively a sodium hydrogen carbonate aqueous solution, deionized water and a saturated sodium chloride aqueous solution. When the solvent of the organic layer is removed, a crude product is obtained. The crude product is purified by a Soxhlet extractor (solvent being hexane), and the remaining solid substance is further extracted with a Soxhlet extractor (using chloroform as a solvent) to obtain 4.54 g of product, which is Ligand-12, and the yield of Ligand-12 is about 82.7%.

Structural analysis and evaluation of the product (Ligand-12) are discussed as follows.

Mass spectrometry analysis (HRMS (FAB)): theoretical value: m/z −986.35 ([M]$^+$); experimental value: m/z −986.2540 ([M]$^+$). $^1$H-NMR spectrum signal (300 MHz, $δ_H$/ppm in d-choloform): 8.77 (4H); 8.12 (4H); 7.93 (2H); 7.60 (2H); 7.51 (8H); 7.43 (2H); 1.47 (36H).

The process flow in synthesizing a ruthenium (Ru)-containing photosensitizer dye (CYC-B6S) is described as follows:

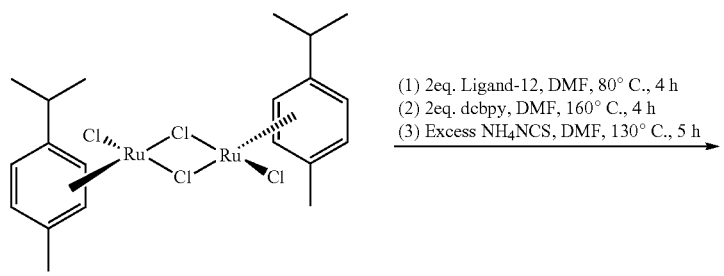

(1) 2eq. Ligand-12, DMF, 80° C., 4 h
(2) 2eq. dcbpy, DMF, 160° C., 4 h
(3) Excess NH$_4$NCS, DMF, 130° C., 5 h -continued

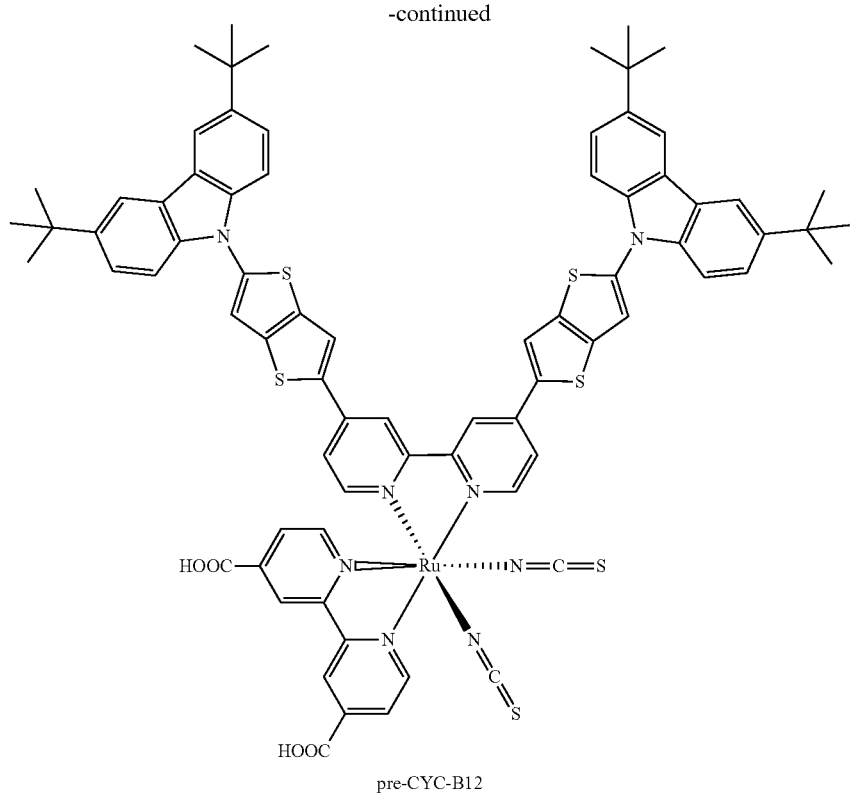

pre-CYC-B12 wherein DMF represents dimethylformamide.

After the Ligand-12 was prepared, 0.456 g of [RuCl$_2$(p-cymene)]$_2$ and 1.5 g of Ligand-12 are dissolved in 125 ml of anhydrous dimethylformamide, and the resulting solution is heated to 80° C. After allowing the reaction to continue for 4 hours, 0.375 g of dcbpy (4,4'-dicarboxylic acid-2,2'-bipyridine) is added. The solution is heated to 160° C. and the reaction is continued for another 4 hours. The subsequent purification procedure of the resulting product is the same as the purification process of CYC-B5, as mentioned above. Thereafter, the product (pre-CYC-B12) of about 2.30 g in weight is obtained, and the yield of pre-CYC-B12 is about 53.2%.

Structural analysis and evaluation of product (pre-CYC-B12) are discussed as follows.

Mass spectrometry analysis (LRMS (FAB)): theoretical value: m/z −1448.26 ([M]$^+$); experimental value: m/z −1449.6 (m) ([M-H]$^+$). (HRMS (FAB)): experimental value: m/z −1448.2581. Elemental analysis of pre-CYC-B12 (C$_{76}$H$_{66}$N$_8$O$_4$S$_6$Ru.H$_2$O) theoretical value: C, 62.23; H, 4.67; N, 7.64%; experimental value: C, 62.00; H, 4.88; N, 7.45%. $^1$H-NMR spectrum signal (500 MHz, $\delta_H$/ppm in d$_6$-DMSO): 9.49 (H); 9.28 (H); 9.23 (H); 9.17 (H); 9.08 (H); 9.01 (H); 8.72 (H); 8.53 (H); 8.36 (H); 8.33 (2 protons); 8.29 (3 protons); 8.06 (H); 8.00 (H); 7.90 (H); 7.69 (H); 7.56 (4 protons); 7.51 (6 protons); 1.43 (18 protons); 1.40 (18 protons).

The method in measuring the absorption coefficient of the photosensitizer dye of the present invention and the comparisons between the absorption position and coefficients of CYC-B5, CYC-B6S, pre-CYC-B12, and various conventional photosensitizer dyes are presented in the following. The method in measuring the absorption coefficient of a photosensitizer dye of the present invention includes providing a photosensitizer dye solution of a known concentration and then placing an appropriate amount of the solution in a quartz sample cell. The sample cell is further placed in a UV/Vis Spectrophotometer for analysis. The absorption coefficient can be calculated by using the Beer's law (A=ϵbc, A: absorbance; ϵ: absorption coefficient; b: beam path; c: concentration of the sample). The absorption coefficients of the photosensitizer dyes of the present invention (CYC-B5, CYC-B6S and pre-CYC-B12) are compared with the absorption coefficients of various conventional photosensitizer dyes, and the results are summarized in Table 1.

It is worthy to note that the conventional photosensitizer dye, "N3", listed in Table 1, is disclosed by M. Grätzel (*J. Photochem. A,* 2004, 164, 3) and M. K. Nazeeruddin et al. (*J. Am. Chem. Soc.* 1993, 115, 6382); the conventional photosensitizer dye, "Black dye", listed in Table 1, is disclosed by M. K. Nazeeruddin et al. (*J. Am. Chem. Soc.,* 2001, 123, 1613); the conventional photosensitizer dye, "Z-910", listed in Table 1, is disclosed by P. Wang, et al. (*Adv. Mater.* 2004, 16, 1806).

TABLE 1

| Photosensitizer Dye | Position of the longest wavelength absorption peak (nm) | Absorption coefficient of the longest wavelength absorption peak (M$^{-1}$ cm$^{-1}$) |
| --- | --- | --- |
| CYC-B5 | 562 | 25100 |
| CYC-B6S | 548 | 16100 |
| pre-CYC-B12 | 555 | 21000 |
| N3 | 530 | 14500 |
| Black dye | 600 | 7640 |
| Z910 | 543 | 16850 |

Based on the results reviewed in Table 1, the absorption coefficient of the photosensitizer dyes CYC-B5, CYC-B6S and pre-CYC-B12 are higher and the absorption wavelength of the photosensitizer dyes CYC-B5, CYC-B6S and pre-CYC-B12 in the present invention are longer than those of the conventional photosensitizer dyes, respectively. Since the photosensitizer dye of the present invention contains the above-mentioned special groups ($X_1$, $X_2$, $Z_1$ and $Z_2$), the photosensitizer dye has a better light absorption capability as compared with the conventional photosensitizer dyes. In other words, a dye-sensitized solar cell using the photosensitizer dye of the present invention can effectively absorb solar light and convert the solar light into an output current.

Additionally, the above detection method is used to obtain an absorption spectra for CYC-B5, CYC-B6S, pre-CYC-B12 and N3, as shown in FIG. 1. Referring to FIG. 1, the curve 110 represents the absorption spectrum of CYC-B5, the curve 120 represents the absorption spectrum of CYC-B6S, and the curve 130 represents the absorption spectrum of pre-CYC-B12, the curve 140 represents the absorption spectrum of N3, and the curve 150 represents the solar spectrum disclosed in Annual Book of ASTM Standard, G159-98 Standard tables for references solar spectral irradiance at air mass 1.5: direct normal and hemispherical for a 37° tilted surface, Vol. 14.04 (2003). As compared with the solar spectrum (curve 150), curves 110, 120 and 130 are closer to the solar spectrum curve 150 than curve 130. In other words, the absorption spectra of CYC-B5, CYC-B6S and pre-CYC-B12 are much closer to the solar spectrum than the absorption spectrum of N3. Accordingly, a dye-sensitized solar cell using the photosensitizer dye of the present invention can effectively absorb solar light and convert the solar light into an output current.

Thereafter, the photosensitizer dyes CYC-B5, CYC-B6S and pre-CYC-B12 of the present invention are respectively used as a material for a dye layer in a dye-sensitized solar cell and the efficiency of the cell is then measured.

The method of forming a dye-sensitized solar cell using respectively CYC-B5, CYC-B6S and pre-CYC-B12 as a material of the dye layer is described as follows. A titanium dioxide ($TiO_2$) electrode submerged in a CYC-B5- or CYC-B6S- or pre-CYC-B12-containing solution for a period of time, such that CYC-B5 or CYC-B6S or pre-CYC-B12 attaches to the surface of the $TiO_2$ electrode in a self-assembly manner.

The $TiO_2$ electrode is removed from the dye-containing solution, and is further rinsed using a solvent and dried. The $TiO_2$ electrode is assembled with a counter electrode, and then the electrodes are sealed with epoxy. After filling with an electrolyte solution and sealing the injection opening, the fabrication of a dye-sensitized solar cell is completed. A dye-sensitized solar cell is fabricated using CYC-B5 or CYC-B6S or pre-CYC-B12 as a material of the dye layer, and thereupon, the voltage, the current and the photoelectric conversion efficiency of the respective cells are measured under irradiation of a virtual sun light with a light source AM1.5G (light intensity of 100 mW/cm$^2$). The results of the measurements are summarized in Table 2.

TABLE 2

| Photosensitizer Dye | Short circuit current density, Jsc (mA/cm$^2$) | Open circuit voltage, Voc (mV) | Fill factor, FF | Photoelectric conversion efficiency, η (%) |
|---|---|---|---|---|
| CYC-B5 | 20.1 | 680 | 0.638 | 8.71 |
| CYC-B6S | 19.8 | 777 | 0.633 | 9.72 |
| pre-CYC-B12 | 14.4 | 731 | 0.636 | 6.72 |

Based on the results presented in Table 2, using CYC-B5 or CYC-B6S or pre-CYC-B12 as a dye to fabricate a dye-sensitized solar cell, the photoelectric conversion efficiency is about 8.71% or 9.72% or 6.72%. The photoelectric conversion efficiency of a dye-sensitized solar cell, in general, ranges between 6% and 10%. That is to say, due to the presence of the special groups ($X_1$, $X_2$, $Z_1$ and $Z_2$) in the photosensitizer dye of the present invention, the solar cell containing the photosensitizer dye of the present invention is provided with excellent photoelectric conversion efficiency.

In view of the above, due to the presence of the special groups ($X_1$, $X_2$, $Z_1$ and $Z_2$) in the photosensitizer dye of the present invention, the absorption spectrum of the photosensitizer dye of the present invention is closer to the solar spectrum and the absorption coefficient of the photosensitizer of the present invention is higher. Moreover, the HOMO and LUMO energy level of the photosensitizer dye in the present invention is compatible well with the oxidation potential of the electrolyte and the conduction band of the anode of a typical dye-sensitized solar cell (DSC). Accordingly, the resulting dye-sensitized solar cell (DSC) of the present invention has higher photoelectric conversion efficiency than the conventional dye-sensitized solar cell (DSC).

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A photosensitizer dye applicable to a dye-sensitized solar cell, wherein the photosensitizer dye is a ruthenium (Ru) complex represented by the following general formula (1), Formula (1):

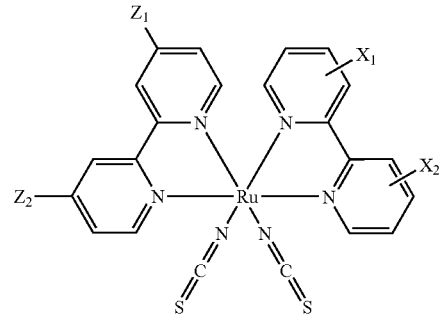

wherein $X_1$ represents one of formula (2) to (19) and $X_2$ represents hydrogen, or $X_1$ and $X_2$ both represent one of formula (2) to (19);

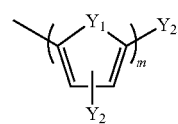

(2)

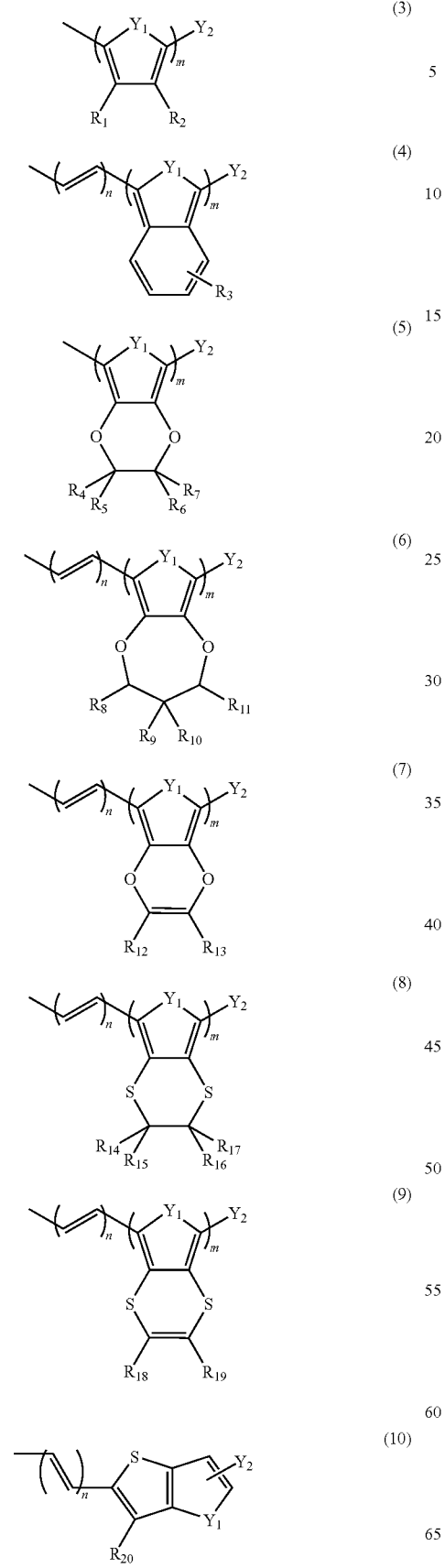
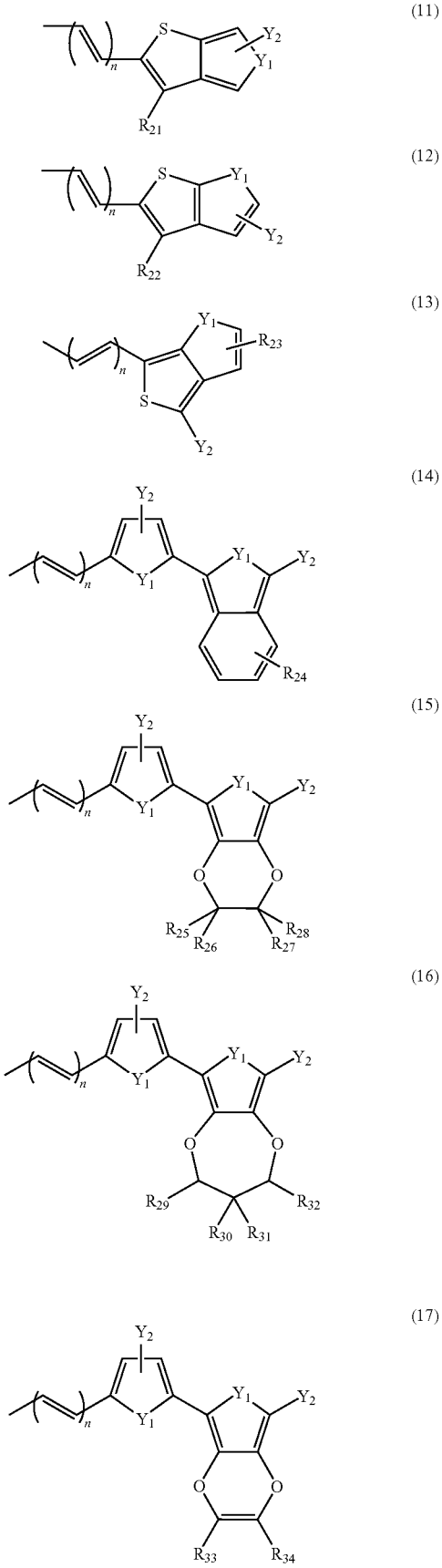

(18)
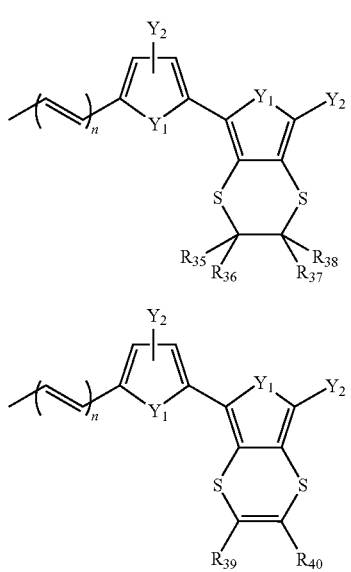
(19)
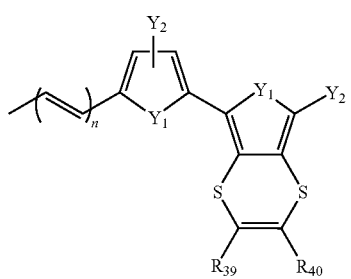
wherein $R_1$ to $R_{40}$ represent independently one of H, $C_tH_{2t+1}$ (t=1 to 15), $OC_vH_{2v+1}$ (v=1 to 15), $SC_wH_{2w+1}$ (w=1 to 15) or formula (36) to (37), and n=0 to 2, m=1 to 4, and wherein $Y_1$ represents one of sulfur (S), methylene group ($CH_2$), amino group (N—R; R represents one of H or $C_xH_{2x+1}$ (x=1 to 15)) or selenium (Se), and $Y_2$ in formula (2)~(19) represents independently one of formula (20) to (37);
—H  (20)
—$C_iH_{2i+1}$  (21)
—O—$C_jH_{2j+1}$  (22)
—S—$C_kH_{2k+1}$  (23)
(24)
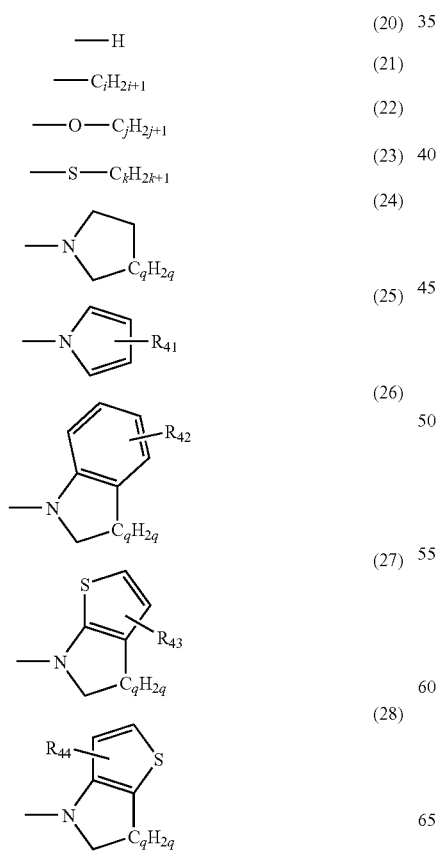
(29)
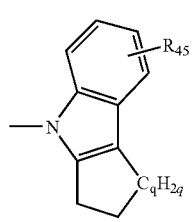
(30)
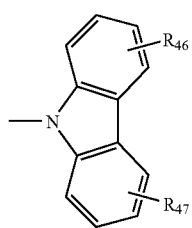
(31)
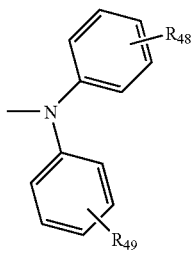
(32)
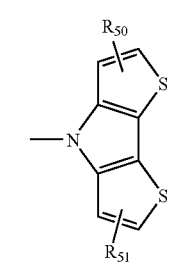
(33)
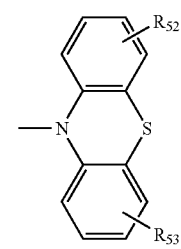
(34)
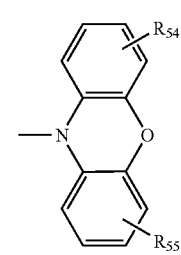

(35)

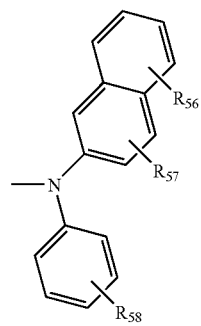

(36)

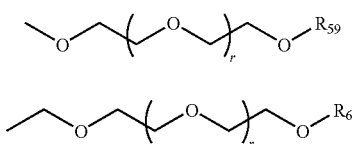

(37)

wherein i=1 to 15 in formula (21), j=1 to 15 in formula (22), and k=1 to 15 in formula (23), wherein $R_{41}$, $R_{42}$, $R_{43}$, $R_{44}$, $R_{45}$, $R_{48}$, $R_{49}$, $R_{50}$, $R_{51}$, $R_{52}$, $R_{53}$, $R_{54}$, $R_{55}$, $R_{56}$, $R_{57}$ and $R_{58}$ independently represent one of H, $C_AH_{2A+1}$ (A=1 to 15), $OC_BH_{2B+1}$ (B=1 to 15), $SC_DH_{2D+1}$ (D=1 to 15) or formula (36) to (37), wherein $R_{46}$ and $R_{47}$ independently represent one of H or $C_EH_{2E+1}$ (E=1 to 6) or $OC_FH_{2F+1}$ (F=1 to 6) or $SC_GH_{2G+1}$ (G=1 to 15), and wherein $R_{59}$ and $R_{60}$ in formula (36) and formula (37) represent independently H or $C_JH_{2J+1}$ (J=1 to 15) and r=0 to 6, wherein q=1 to 3 of $C_qH_{2q}$ in formula (24), formula (26), formula (27), formula (28) and formula (29);

wherein $Z_1$ represents one of formula (38) to (44), and $Z_2$ represents hydrogen or one of formula (38) to (44) or a group the same as $Z_1$;

—COOA$_1$ (38)

—PO$_3$HA$_1$ (39)

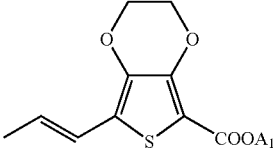 (40)

(41)

(42)

(43)

(44)

wherein $R_{61}$ and $R_{62}$ independently represent one of H, $C_IH_{2I+1}$ (I=1 to 15), $OC_JH_{2J+1}$ (J=1 to 15) or $SC_KH_2K+1$ (K=1 to 15);

wherein $A_1$ represents hydrogen (H), lithium (Li), sodium (Na), potassium (K), tetra-alkyl ammonium groups as represented by general formula (45), or any species or groups with positive charge;

(45)

$$R_{66}-\overset{R_{63}}{\underset{R_{65}}{\overset{\oplus}{N}}}-R_{64}$$

wherein $R_{63}$, $R_{64}$, $R_{65}$ and $R_{66}$ independently represent H or $C_yH_{2y+1}$ (y=1 to 15);

when $Z_1$ and $Z_2$ both represent formula (38) and $X_1$ represents formula (2) and $Y_1$ in formula (2) represents sulfur (S) and $X_2$ represents hydrogen or a group the same as $X_1$ (formula (2)), $Y_2$ does not represent one of formula (20)~(22) or formula (31) wherein one of $Y_2$ in formula (2) merely represents one of formula (23)~(30) or one of formula (32)~(37);

when $Z_1$ and $Z_2$ both represent formula (38) and $X_1$ represents formula (3) and $Y_1$ in formula (3) represents sulfur (S) and $X_2$ represents hydrogen or a group the same as $X_1$ (formula (3)), $Y_2$ does not represent one of formula (20)~(22) or formula (31) wherein $Y_2$ merely represents one of formula (23)~(30) or one of formula (32) (37);

when $Z_1$ and $Z_2$ both represent formula (38) and $X_1$ represents formula (4) and n in formula (4) represents 0 and $Y_1$ in formula (4) represents sulfur (S) and $R_3$ in formula (4) represents hydrogen (H) and $X_2$ represents hydrogen or a group the same as $X_1$ (formula (4)), $Y_2$ does not represent one of formula (20)~(22) wherein $Y_2$ merely represents one of formula (23)~(37);

when $Z_1$ and $Z_2$ both represent formula (38) and $X_1$ represents formula (5) and $Y_1$ in formula (5) represents sulfur (S) and $R_4$~$R_7$ in formula (5) represent hydrogen (H) and $X_2$ represents hydrogen or a group the same as $X_1$ (formula (5)), $Y_2$ does not represent one of formula (20)~(22) wherein $Y_2$ merely represents one of formula (23)~(37), when $Z_1$ and $Z_2$ both represent formula (38) in which $A_1$ represents hydrogen (H) and $X_1$ and $X_2$ both represent formula (10) or formula (12) in which n=0 and $Y_1$ represents sulfur (S), $Y_2$ in formula (10) or formula (12) does not represent one of formula (20)~(23) wherein $Y_2$ merely represents one of formula (24)~(37).

2. The photosensitizer dye according to claim 1, wherein a structure of the photosensitizer dye is represented by the following formula (61) to (67),

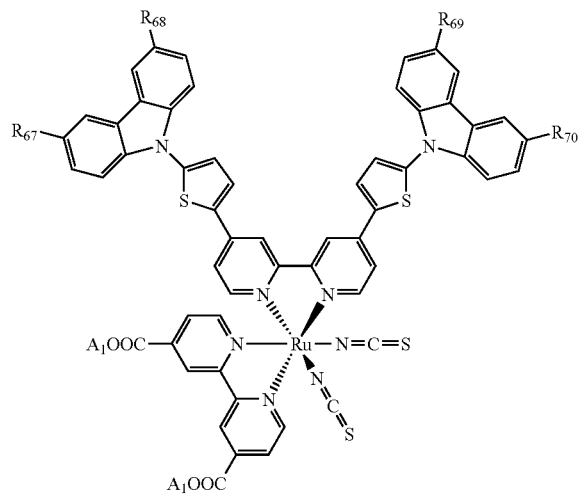
(61)
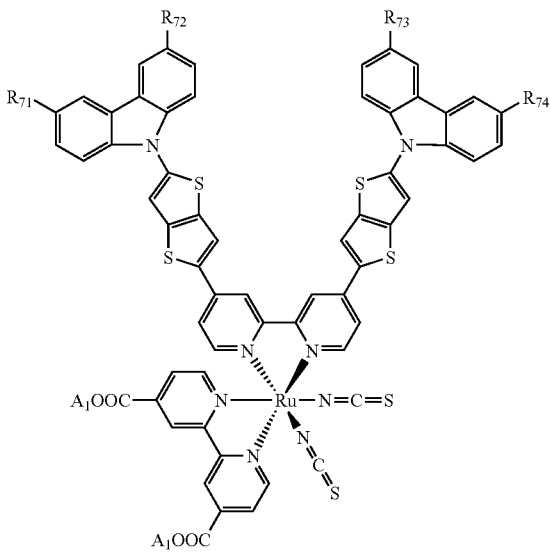
(62)
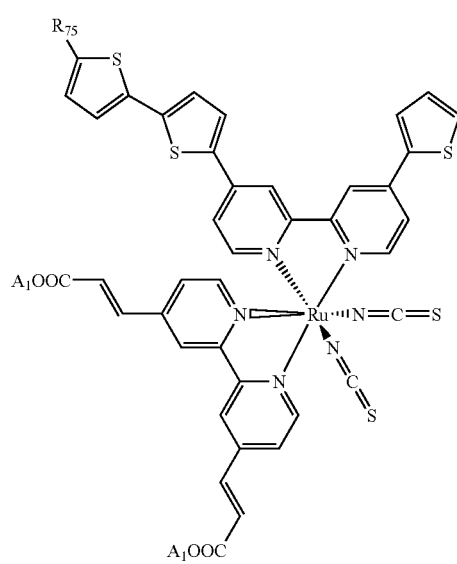
(63)
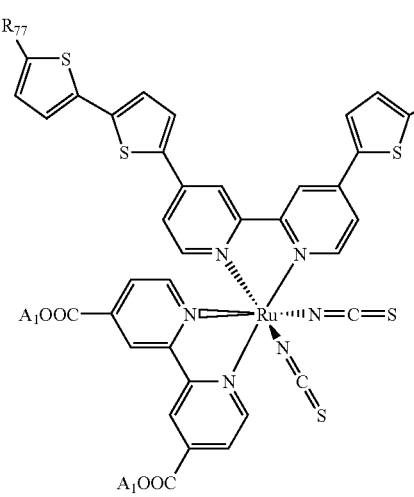
(64)
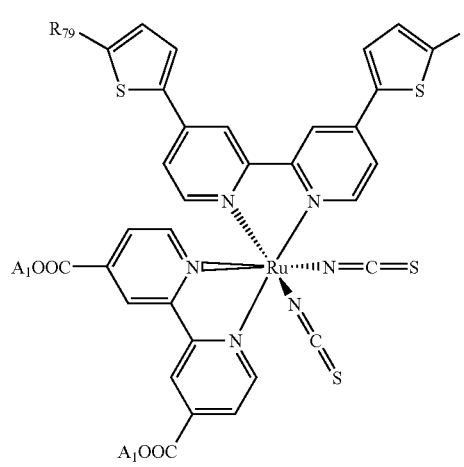
(65)
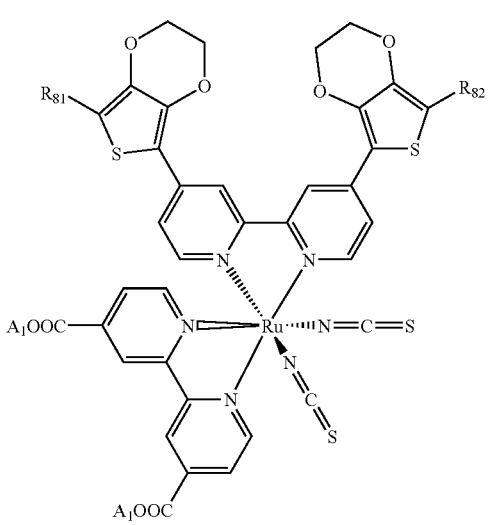
(66)

(67)

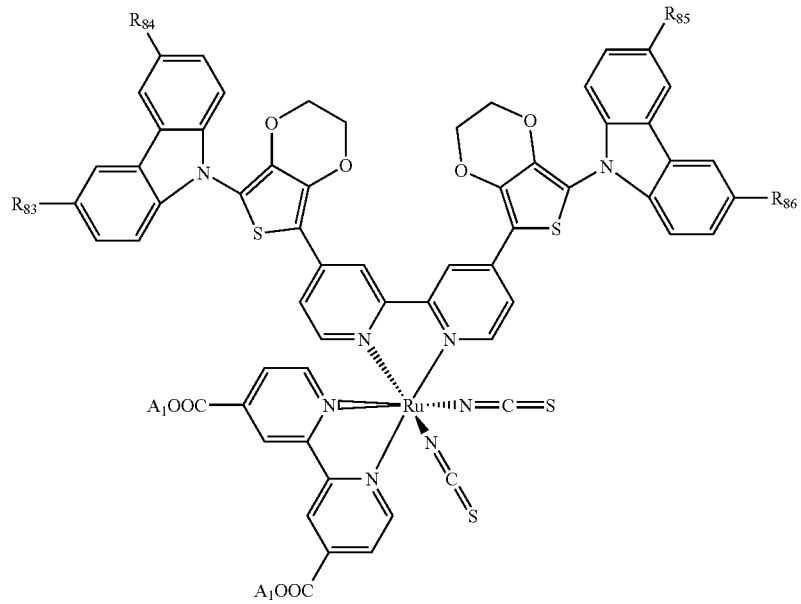

wherein $R_{67}$, $R_{68}$, $R_{69}$ and $R_{70}$ independently represent one of H, $C_EH_{2E+1}$ (E=1 to 6), $OC_FH_{2F+1}$ (F=1 to 6), $SC_GH_{2G+1}$ (G=1 to 15) or formula (36) to (37);

wherein $R_{71}$, $R_{72}$, $R_{73}$ and $R_{74}$ independently represent one of H, $C_AH_{2A+1}$ (A=1 to 15), $OC_BH_{2B+1}$ (B=1 to 15), $SC_DH_{2D+1}$ (D=1 to 15) or formula (36) to (37);

wherein $R_{75}$ and $R_{76}$ independently represent one of H, $C_tH_{2t+1}$ (t=1 to 15), $OC_vH_{2v+1}$ (v=1 to 15), $SC_wH_{2w+1}$ (w=1 to 15) or formula (36) to (37);

wherein $R_{77}$, $R_{78}$, $R_{79}$, $R_{80}$, $R_{81}$ and $R_{82}$ independently represent one of $SC_GH_{2G+1}$ (G=1 to 15) or formula (36) to (37);

wherein $R_{83}$, $R_{84}$, $R_{85}$ and $R_{86}$ independently represent one of H, $C_AH_{2A+1}$ (A=1 to 15), $OC_BH_{2B+1}$ (B=1 to 15), $SC_DH_{2D+1}$ (D=1 to 15) or formula (36) to (37);

wherein $A_1$ independently represents hydrogen (H), lithium (Li), sodium (Na), potassium (K) or tetra-alkyl ammonium groups as represented by general formula (45);

(45)

wherein $R_{63}$, $R_{64}$, $R_{65}$ and $R_{66}$ independently represent H or $C_yH_{2y+1}$ (y=1 to 15).

3. The photosensitizer dye according to claim 2, wherein a structure of the photosensitizer dye is represented by the following formula (68) to (74), (68)

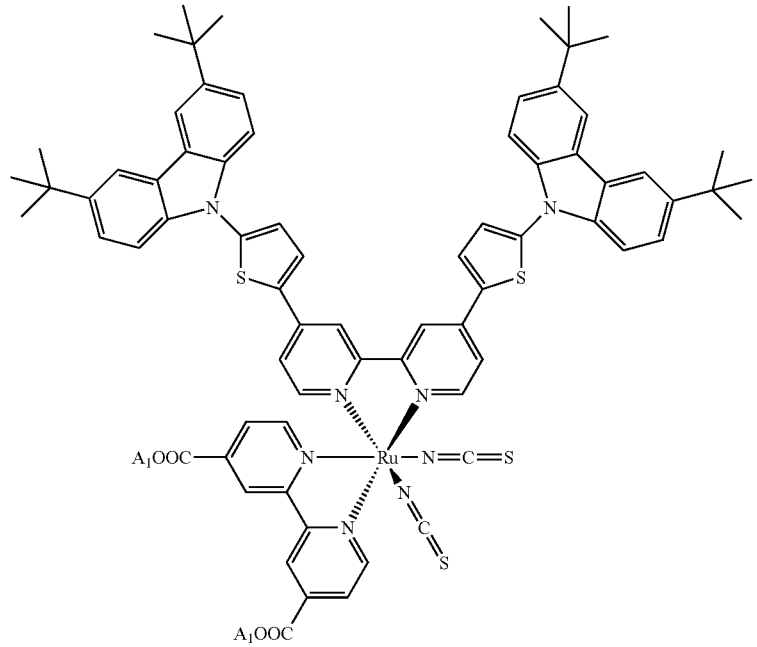

-continued
(69)
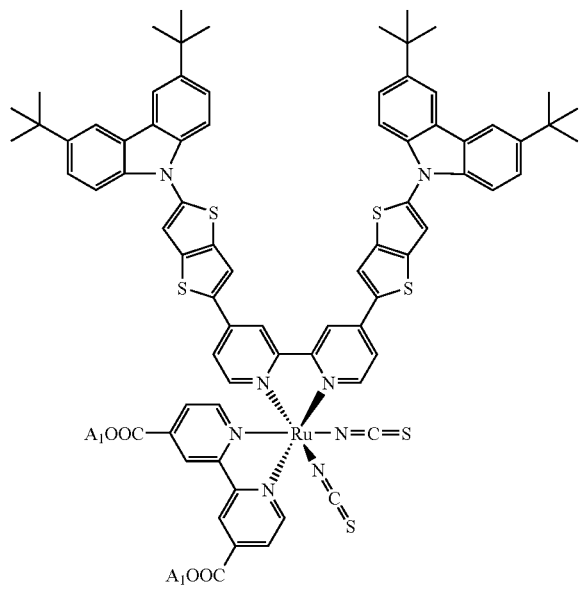
(70)
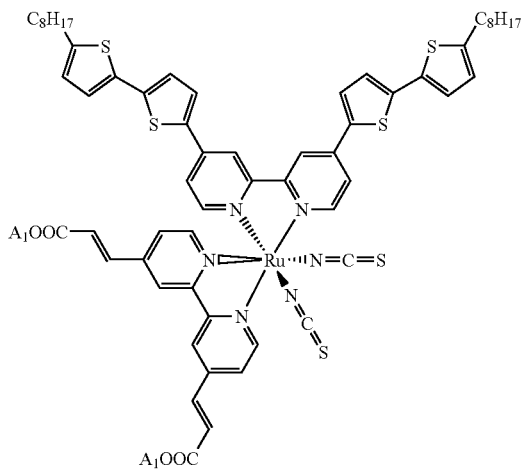
(71)
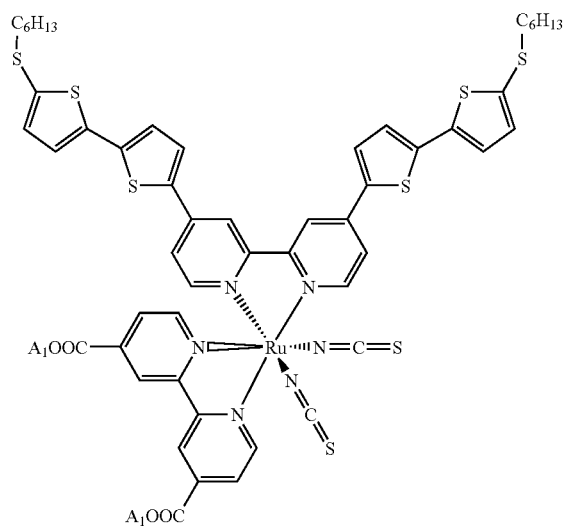
(72)
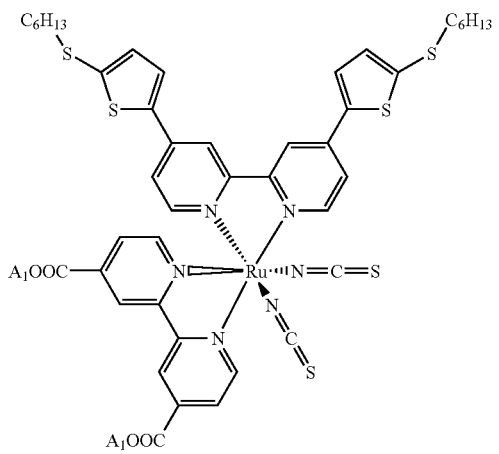
(73)
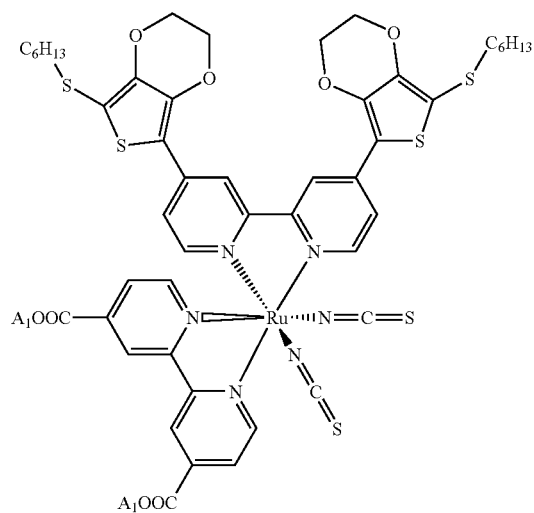

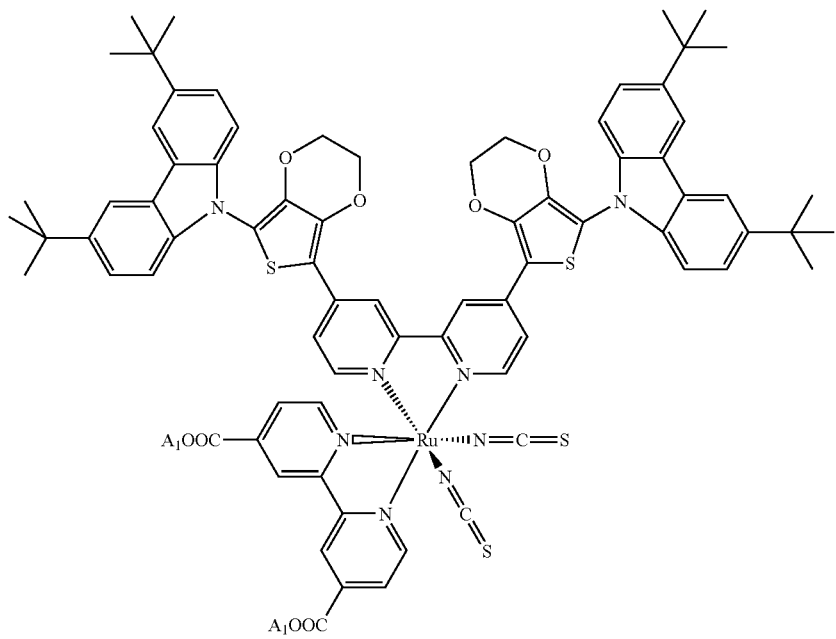
(74)
wherein $A_1$ independently represents hydrogen (H), lithium (Li), sodium (Na), potassium (K) or tetra-alkyl ammonium groups as represented by general formula (45);
(45)
wherein $R_{63}$, $R_{64}$, $R_{65}$ and $R_{66}$ independently represent H or $C_yH_{2y+1}$ (y=1 to 15).
4. The photosensitizer dye according to claim 2, wherein a structure of the photosensitizer dye is represented by the following formula (75) to (76),
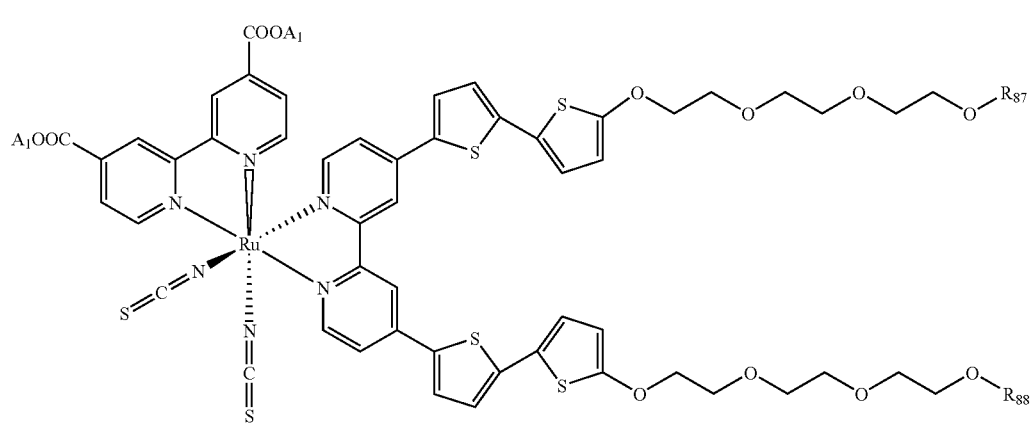
(75)

(76)
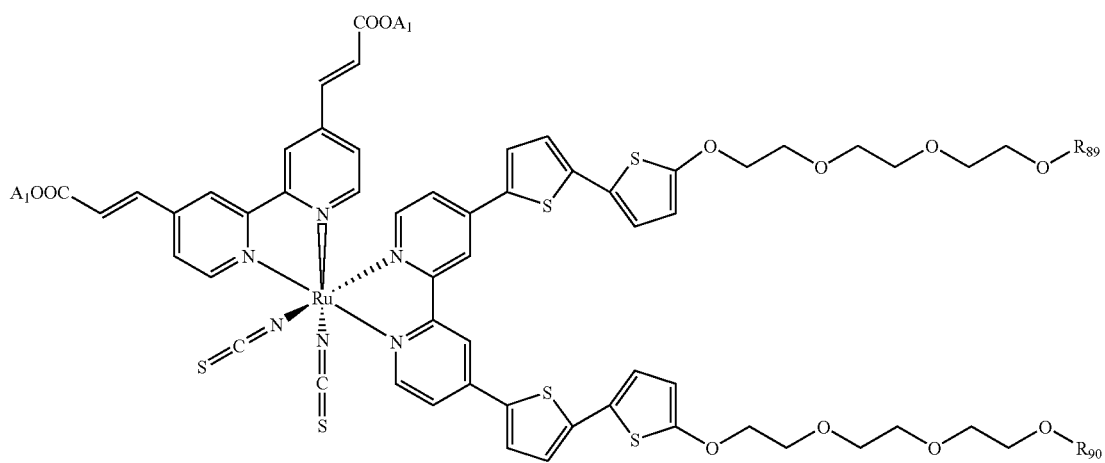
wherein $R_{87}$, $R_{88}$, $R_{89}$ and $R_{90}$ independently represent one of H or $C_JH_{2J+1}$ (J=1 to 15);
wherein $A_1$ independently represents hydrogen (H), lithium (Li), sodium (Na), potassium (K) or tetra-alkyl ammonium groups as represented by general formula (45);
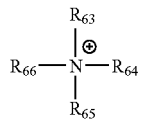
(45)
wherein $R_{63}$, $R_{64}$, $R_{65}$ and $R_{66}$ independently represent H or $C_yH_{2y+1}$ (y=1 to 15).
* * * * *